United States Patent [19]
Goulait et al.

[11] Patent Number: 5,392,498
[45] Date of Patent: Feb. 28, 1995

[54] NON-ABRASIVE SKIN FRIENDLY MECHANICAL FASTENING SYSTEM

[75] Inventors: David J. K. Goulait; Dennis A. Thomas, both of Cincinnati, Ohio

[73] Assignee: The Proctor & Gamble Company, Cincinnati, Ohio

[21] Appl. No.: 988,636

[22] Filed: Dec. 10, 1992

[51] Int. Cl.6 .............................................. A44B 18/00
[52] U.S. Cl. ......................................... 24/452; 24/446; 24/450
[58] Field of Search ................ 24/452, 451, 450, 449, 24/448, 447, 446, 445, 443, 442, 306

[56] References Cited

U.S. PATENT DOCUMENTS

| | | |
|---|---|---|
| 392,363 | 11/1888 | Riggs . |
| 569,213 | 10/1896 | Lehnig . |
| 625,022 | 5/1899 | Crist . |
| 2,717,437 | 9/1955 | Mestral .............................. 28/72 |
| 3,057,354 | 10/1962 | Roberts et al. . |
| 3,130,111 | 4/1964 | Izumi .................................. 161/48 |
| 3,147,528 | 9/1964 | Erb ..................................... 24/204 |
| 3,266,113 | 8/1966 | Flanagan, Jr. ..................... 24/204 |
| 3,426,400 | 2/1969 | Lauro ................................. 24/255 |
| 3,461,513 | 8/1969 | Girard et al. ...................... 24/204 |
| 3,536,518 | 10/1970 | Drelich .............................. 117/38 |
| 3,550,223 | 12/1970 | Erb ..................................... 24/204 |
| 3,550,837 | 12/1970 | Erb ..................................... 229/45 |
| 3,557,407 | 1/1971 | Lemelson ........................... 425/71 |
| 3,562,044 | 2/1972 | Erb ..................................... 156/155 |
| 3,594,863 | 7/1971 | Erb ..................................... 18/5 |
| 3,594,865 | 7/1971 | Erb ..................................... 18/5 |
| 3,629,032 | 12/1971 | Erb ..................................... 156/196 |
| 3,643,316 | 2/1972 | Girard et al. ...................... 29/400 |
| 3,675,571 | 7/1972 | Vertegaal . |
| 3,708,382 | 1/1973 | Erb ..................................... 161/48 |
| 3,708,833 | 1/1973 | Ribich et al. ..................... 24/204 |
| 3,943,981 | 3/1976 | De Brabander .................... 139/391 |
| 4,056,593 | 11/1977 | de Navas Albareda ............ 264/145 |
| 4,169,303 | 10/1979 | Lemelson ........................... 24/204 |
| 4,198,734 | 4/1980 | Brumlik .............................. 24/204 |
| 4,216,257 | 8/1980 | Schams et al. ..................... 428/93 |
| 4,307,493 | 12/1981 | Ochiai ................................ 24/204 |
| 4,330,907 | 5/1982 | Ochiai ................................ 24/204 |
| 4,454,183 | 6/1984 | Wollman ............................ 428/92 |
| 4,462,784 | 7/1984 | Russell .............................. 425/223 |
| 4,463,486 | 8/1984 | Matsuda ............................ 28/161 |
| 4,532,157 | 7/1985 | Schmidt et al. ................... 427/262 |
| 4,562,099 | 12/1985 | Hichcliffe ......................... 427/282 |

(List continued on next page.)

FOREIGN PATENT DOCUMENTS

| | | |
|---|---|---|
| 2027159 | 7/1991 | Canada . |
| 0276970 | 8/1988 | European Pat. Off. . |
| 0325473A1 | 7/1989 | European Pat. Off. . |
| 0353972 | 2/1990 | European Pat. Off. . |
| 0381087 | 8/1990 | European Pat. Off. . |
| 0388681 | 9/1990 | European Pat. Off. . |
| 0476992A1 | 3/1992 | European Pat. Off. . |
| 0491347A1 | 6/1992 | European Pat. Off. . |
| 1551245 | 12/1968 | France . |
| 2432108 | 12/1980 | France ............................... 3/16 |
| 55/137942 | 10/1980 | Japan . |
| 1437005 | 5/1976 | United Kingdom ................ 24/451 |
| 2233876A | 1/1991 | United Kingdom . |
| WO87/06522 | 11/1987 | WIPO . |

Primary Examiner—Victor N. Sakran
Attorney, Agent, or Firm—Steven W. Miller; E. Kelly Linman; Jacobus C. Rasser

[57] ABSTRACT

The invention is a hook fastening material for use with a complementary loop fastening material, which hook fastening material has from about 1600 to about 2500 prongs per square inch and is substantially non-abrasive and non-irritating to human skin. In one embodiment the hook fastening material has prongs with an engaging means at an angle of about 90° to about 160° relative to the extension of the perpendicular to the plane of the substrate. In another embodiment the hook fastening material is formed on a compressible substrate. In still another embodiment the hook fastening material has prongs made of an ethylene vinyl acetate based polymer or a polyethylene based polymer. Methods for making such hook fastening materials and articles of use are also disclosed.

10 Claims, 7 Drawing Sheets

U.S. PATENT DOCUMENTS

| | | | |
|---|---|---|---|
| 4,587,152 | 5/1986 | Gleichenhagen | 428/195 |
| 4,672,893 | 6/1987 | Mammarella, Sr. | 101/170 |
| 4,699,622 | 10/1987 | Toussant et al. | 604/389 |
| 4,725,221 | 2/1988 | Blanz | 425/575 |
| 4,776,068 | 10/1988 | Smirlock et al. | 24/442 |
| 4,794,028 | 12/1988 | Fischer | 428/100 |
| 4,829,641 | 5/1989 | Williams | 24/587 |
| 4,846,815 | 7/1989 | Scripps . | |
| 4,869,724 | 9/1989 | Scripps . | |
| 4,876,982 | 10/1989 | Claassen . | |
| 4,894,060 | 1/1990 | Nestegard | 604/91 |
| 4,920,617 | 5/1990 | Higashinaka | 24/446 |
| 4,938,835 | 7/1990 | Ludwig | 118/68 |
| 4,963,140 | 10/1990 | Robertson . | |
| 4,973,326 | 11/1990 | Wood et al. | 604/391 |
| 4,984,339 | 1/1991 | Provost et al. | 24/452 |
| 5,013,498 | 5/1991 | Froeschke . | |
| 5,019,065 | 5/1991 | Scripps . | |
| 5,040,275 | 8/1991 | Eckhardt et al. . | |
| 5,053,028 | 10/1991 | Zoia et al. . | |
| 5,058,247 | 10/1991 | Thomas et al. . | |
| 5,116,563 | 5/1992 | Thomas et al. | 156/66 |
| 5,122,219 | 6/1992 | Ludwig | 156/244.17 |
| 5,131,119 | 7/1992 | Murasaki et al. . | |
| 5,135,522 | 8/1992 | Fahrenkrug et al. . | |
| 5,180,534 | 1/1993 | Thomas et al. . | |
| 5,231,738 | 8/1993 | Higashinaka | 24/450 |

5,392,498

NON-ABRASIVE SKIN FRIENDLY MECHANICAL FASTENING SYSTEM

FIELD OF THE INVENTION

The present invention relates to hook and loop type refastenable mechanical fastening systems, more particularly to refastenable mechanical fastening systems having free-formed prongs and the process of manufacturing such fastening systems.

BACKGROUND OF THE INVENTION

Hook and loop type mechanical fastening systems are well known in the art. Such fastening systems involve two major components, a hook fastening material and a loop fastening material. The hook fastening material comprises an array of engaging elements or prongs, joined to a substrate. The engaging elements are intended to engage a complementary receiving surface such as a loop fastening material. Generally, loop fastening materials will comprise loops, fibers, or the like with which the engaging elements of the hook fastening material can become entangled.

Hook fastening materials are generally irritating and abrasive to human skin, and, therefore, not suitable for applications where the fastening system will be positioned in proximity to human skin. There is, therefore, a need for a hook fastening material which is non-irritating and non-abrasive to human skin, i.e., "skin-friendly". Such a skin-friendly mechanical fastening system would be particularly useful on products such as sanitary napkins, disposable diapers, incontinent garments, and the like.

Accordingly, it is an object of the present invention to provide a skin friendly mechanical fastening system that may be used in applications which puts the mechanical fastening system in proximity to human skin.

It is also an object of the present invention to provide a method of producing such fastening systems.

SUMMARY OF THE INVENTION

The present invention relates to a hook fastening material for use as a component of a mechanical fastening system. The hook fastening material comprises a substrate and an array of prongs, each prong comprising a base, a shank, and an engaging means. Each of the prongs additionally is comprised of an ethylene vinyl acetate based polymer. In a preferred embodiment the array of prongs will comprise from about 1,600 to about 2,500 prongs per square inch.

In a particularly preferred embodiment of the present invention the prongs will additionally have a substantially constant diameter shank. In the most preferred embodiment the fastening material will additionally comprise a compressible substrate.

An illustrative and suitable, but nonlimiting, use for the fastening system produced by the process of the present invention is in conjunction with a disposable absorbent article, such as a diaper. This example of one usage of the fastening system of the present invention is more fully described herein.

BRIEF DESCRIPTION OF THE DRAWINGS

While the Specification concludes with claims particularly pointing out and distinctly claiming the invention, it is believed the invention will be better understood from the following description taken in conjunction with the associated drawings in which like elements are described by the same reference numeral or letter and related elements are designated by adding one or more prime symbols or incrementing the numerals by 100:

DETAILED DESCRIPTION OF THE INVENTION

Figure 1:
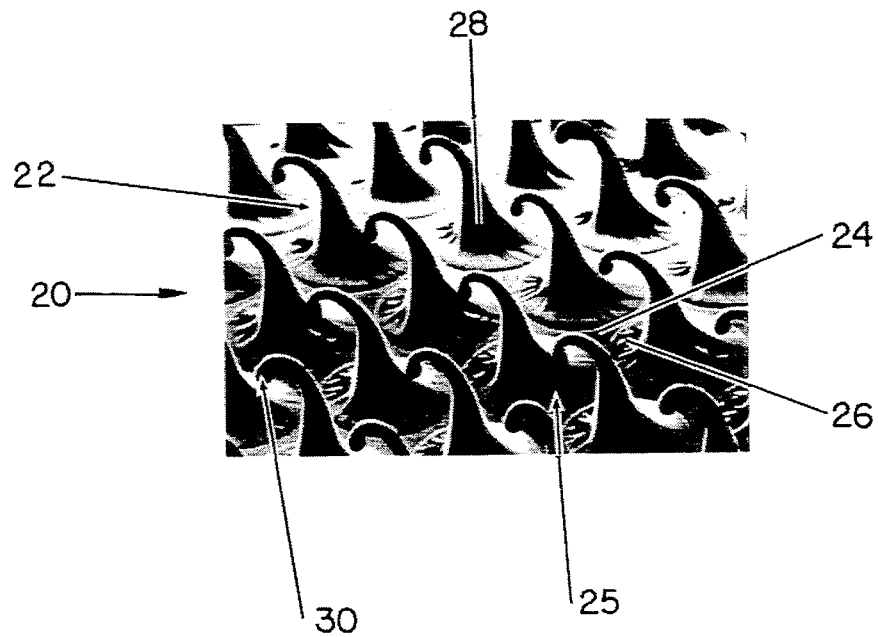
FIG. 1 is a photomicrograph showing a perspective view of a fastening system of the present invention wherein the engaging means are oriented in substantially the same direction.

The mechanical fastening system 20 of the present invention comprises at least one prong 22, and preferably an array of prongs 22, joined to a substrate 24 in a predetermined pattern as shown in FIG. 1. The prongs 22 have a base 26, shank 28 and engaging means 30. The bases 26 of the prongs 22 contact and adhere to the substrate 24, and support the proximal ends of the shanks 28. The shanks 28 project outwardly from the substrate 24 and bases 26. The shanks 28 terminate at a distal end which is joined to an engaging means 30. The engaging means 30 project laterally from the shanks 28 in one or more directions and may resemble a hook-shaped tine. As used herein, the term "lateral" means having a vector component generally parallel to the plane of the substrate 24. The projection of an engaging means 30 from the shank 28 periphery in a lateral direction allows the engaging means 30 to be secured to a complementary receiving surface (not shown). The engaging means 30 is joined to, and preferably contiguous with, the distal end of the shank 28.

The array of prongs 22 is produced by a method which yields a free formed prong 22 as described and claimed hereinbelow. As used herein, the term "free formed" means a structure which is not removed from a mold cavity or extrusion die in solid form or with a defined shape. The prongs 22 are deposited onto a substrate 24 which will be discussed in detail hereinbelow, in a molten, preferably liquid state and solidified, by cooling until rigid and preferably freezing, into the desired structure and shape as described hereinafter.

Figure 4:
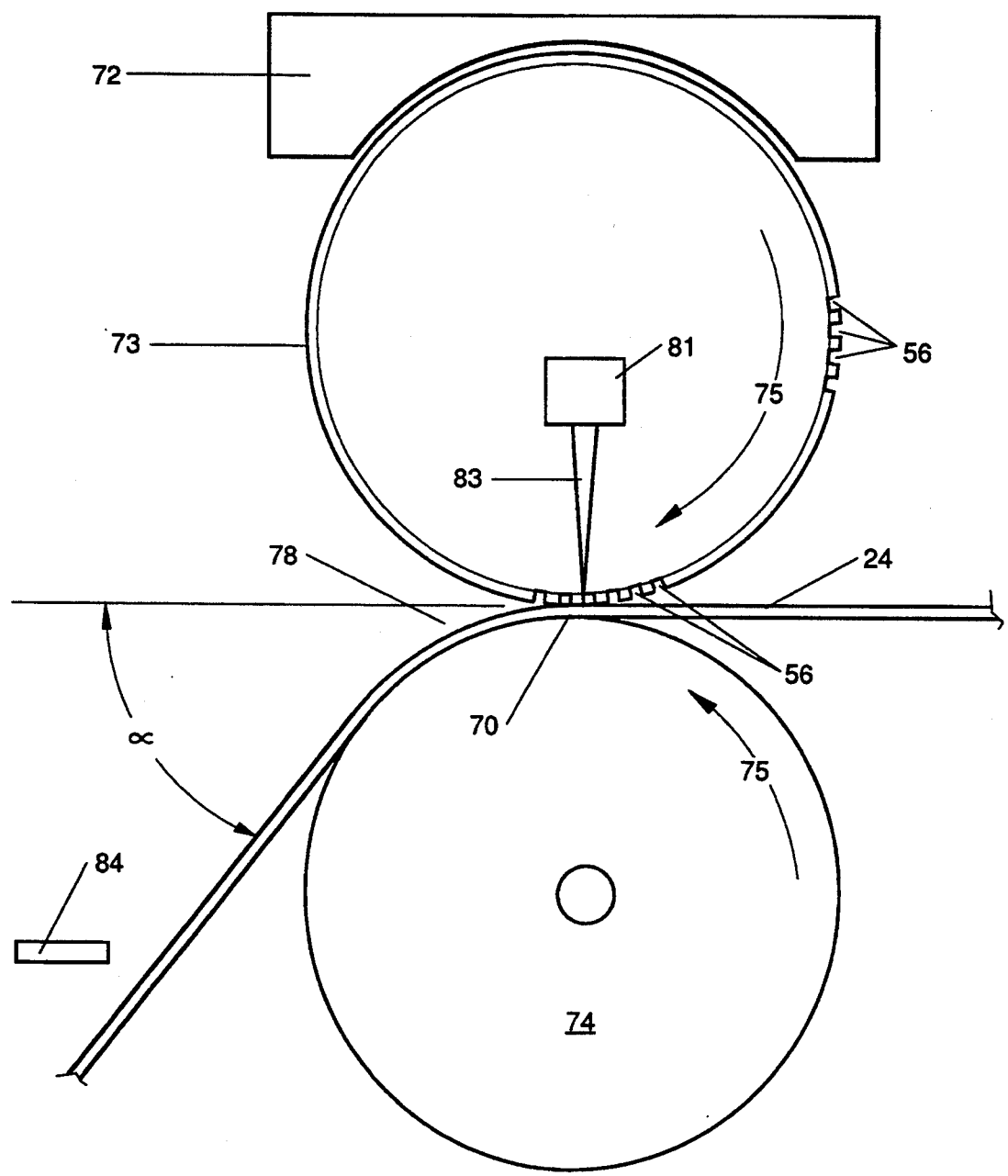
FIG. 4 is a side elevational schematic view of a screen printing apparatus used to produce the fastening system of the present invention.

The free formed array of prongs 22 is preferably produced by a manufacturing process which is similar to that process commonly known as rotary screen printing. This process uses a depositing member in the form of a generally cylindrical screen, referred to as the print cylinder 73. Using this process, a substrate 24 having opposed faces is passed between the nip 70 of the print cylinder 73 and a backing roll 74, as illustrated at FIG. 4. The print cylinder 73 and backing roll 74 have generally parallel centerlines and are maintained in contacting relationship with the substrate 24 as it passes through the nip 70. The depositing member, presently referred to as the print cylinder 73, has an array of perforations, referred to as apertures 56, corresponding to the desired pattern of prongs 22 to be deposited on the substrate 24. The second roll, referred to as the backing roll 74, provides the reaction against the print cylinder 73 to position the substrate 24 against the print cylinder 73 as the substrate 24 passes through the nip 70. Liquid, thermally sensitive material, preferably thermoplastic material, from which the prongs 22 are to be formed is supplied from a heated source, such as a heated pressure bar 81. The thermally sensitive material is forced into the apertures 56 by a doctor blade 83 as the print cylinder 73 is rotated about its centerline. The thermally sensitive material is then extruded from the apertures 56 onto the substrate 24 in the desired pattern.

As relative displacement between the substrate 24 and print cylinder 73 increases, the prongs 22 are stretched in a direction having a lateral vector component, generally parallel to the plane of the substrate 24, forming the shank 28 and the engaging means 30. Finally, the moil of the prong 22 is severed from the engaging means 30 by a severing means 78. Due to the viscoelastic properties of the thermoplastic, the prong 22 retracts. It is also believed that the prong 22 retracts under the influences of gravity and shrinkage which occur during cooling. The prong 22 then cools, and preferably freezes, into a solid structure having the engaging means 30 contiguous with the shank 28.

The fastening system 20 is secured to a complementary receiving surface. As used herein, the term "receiving surface" to which the engaging means 30 of the fastening system 20 are secured refers to any plane or surface having an exposed face with tightly spaced openings complementary to the engaging means 30 and defined by one or more strands or fibers or, alternatively, which exposed face is capable of localized elastic deformation so that the engaging means 30 may become entrapped and not withdrawn without interference. The openings or localized elastic deformations allow for entry of the engaging means 30 into the plane of the receiving surface, while the strands (or nondeformed material) of the receiving surface interposed between the openings (or deformed areas) prevent withdrawal or release of the fastening system 20 until desired by the user or either the peel or shear strength of the fastening system 20 is otherwise exceeded. The plane of the receiving surface may be flat or curved.

A receiving surface having strands or fibers, is said to be "complementary" if the openings between strands or fibers are sized to allow at least one engaging means 30 to penetrate into the plane of the receiving surface, and the strands are sized to be engaged or intercepted by the engaging means 30. A receiving surface which is locally deformable is said to be "complementary" if at least one engaging means 30 is able to cause a localized disturbance to the plane of the receiving surface, which disturbance resists removal or separation of the fastening system 20 from the receiving surface.

Suitable receiving surfaces include reticulated foams, knitted fabrics, woven and nonwoven materials, and stitchbonded loop materials, such as Velcro brand loop materials sold by Velcro USA of Manchester, N.H. A particularly suitable receiving surface is a polypropylene non-woven fabric having a basis weight of about 17.1 grams per square meter (0.5 ounces per square yard) made by any suitable commercial carding or spunbonding processes. Suitable non-woven fabrics can be obtained from Veratec Nonwoven Group of the International Paper Company of Walpole, Mass. 02081. Other receiving surfaces may also be used, such as stitchbonded fabric Number 970026 sold by the Milliken Company of Spartanburg, S.C.

Referring back to FIG. 2 to examine the components of the fastening system 20 in more detail, the substrate 24 of the fastening system 20 should be strong enough to preclude tearing and separation between individual prongs 22 of the fastening system 20, be a surface to which the prongs 22 will readily adhere and be capable of being joined to an article to be secured as desired by a user. As used herein the term "join" refers to the condition where a first member, or component, is affixed, or connected to a second member or component, either directly; or indirectly, where the first member or component is affixed or connected to an intermediate member, or component which in turn is affixed, or connected, to the second member or component. The association between the first member, or component, and the second member, or component, is intended to remain for the life of the article. The "substrate" is any exposed surface to which one or more prongs 22 are joined.

The substrate 24 should also be capable of being rolled, to support conventional manufacturing processes, flexible so that the substrate 24 may be bent or flexed in a desired configuration, and able to withstand the heat of the liquid prongs 22 being deposited thereon without melting or incurring deleterious effects until such prongs 22 freeze. However, the backing roll 74 may be chilled, allowing the process to accommodate substrates 24 which otherwise would not be able to withstand the heat of the liquid prongs 22. The substrate 24 should also be available in a variety of widths. Suitable substrates 24 include knitted fabric, woven materials, nonwoven materials, rubber, vinyl, films, particularly polyolefinic films and preferably polyester films. A polyester film substrate 24 having a basis weight of 17.1 grams per square meter (14.26 grams per square yard) and a thickness of about 0.008 to about 0.15 millimeters (0.0003 to 0.006 inches) has been found suitable. Such materials are commercially available from Hoechst Celanese of Greer, S.C., 29651 and sold under the trade name Hostaphan 2400 polyester film. (More rigid substrates, such as cardboard and the like, may also be used.)

The base 26 is the generally planar portion of the prong 22 which is attached to the substrate 24 and is contiguous with the proximal end of the shank 28 of the prong. As used herein, the term "base" refers to that portion of the prong 22 which is in direct contact with the substrate 24 and supports the shank 28 of the prong 22. It is not necessary that a demarcation be apparent between the base 26 and the shank 28. It is only important that the shank 28 not separate from the base 26 and that the base 26 not separate from the substrate 24 during use. The base 26 cross section should provide sufficient structural integrity, and hence area, for the desired peel and shear strengths of the fastening system 20, based on the density of the pattern of prongs 22 and the geometry of the shank 28 and engaging means 30 and further provide adequate adhesion to the substrate 24. If a longer shank 28 is utilized, the base 26 should generally be of greater cross sectional area to provide sufficient adhesion to the substrate 24 and adequate structural integrity.

The shape of the footprint of the base 26 on the substrate 24 generally corresponds to the shape of the aperture's sectional area at the surface of the print cylinder 73. As used herein, the term "footprint" refers to the planar contact area of the base 26 on the substrate 24. As the aspect ratio of the sides of the footprint increases, the prong 22 may become unstable when subjected to forces, such as gravitational forces, parallel to the shorter dimension of the footprint. To produce a prong 22 which is oriented substantially in the machine direction of the substrate 24, an aspect ratio of less than about 1.5:1 is preferred, and a generally circular footprint is more preferred. However, to produce azimuthally angled prongs 22, i.e. prongs oriented in a direction other than the machine direction, an aspect ratio greater than about 1.5:1 is preferred, and a generally elliptical or triangular footprint having an aspect ratio greater than about 1.5:1 is even more preferred. Methods of producing azimuthally angled prongs will be discussed in greater detail hereinbelow.

For the embodiment described herein, a base 26 having a footprint of generally circular shape and approximately 0.10 millimeters to 0.30 millimeters (0.004 to 0.012 inches) in diameter is suitable. If it is desired to make the fastening system 20 have a greater peel or shear strength in a particular direction, the cross sectional area of the base 26 may be modified to amplify such direction, so that the strength and structural integrity relative to the axis parallel to such direction increases. This modification causes the prongs 22 to be stronger when pulled in the amplified direction of the base 26.

The shank 28 is contiguous with the base 26 and projects outwardly from the base 26 and substrate 24. As used herein, the term "shank" refers to that portion of the prong 22 which is intermediate of and contiguous with the base 26 and the engaging means 30. The shank 28 provides longitudinal spacing of the engaging means 30 from the substrate 24. As used herein, the term "longitudinal" means in a direction having a vector component away from the substrate 24, which direction increases the perpendicular distance to the plane of the substrate 24 at the base 26 of the prong 22, unless otherwise specified to be a direction having a vector component towards such plane of the substrate 24.

Associated with the shank 28 and base 26 of each prong 22 is an origin 36. The "origin" of the shank 28 is the point which may be thought of as the center of the base 26, and is typically within the footprint of the base 26. The origin 36 is found by viewing the prong 22, from the side view. The "side view" is any direction radially towards the shank 28 and base 26 which is also parallel to the plane of the substrate 24.

The lateral distance between the remote edges of the base 26 footprint for the particular side view under consideration is found, and this distance is bisected, yielding the midpoint of the base 26 for such view. When bisecting the footprint of the base 26 for the particular side view under consideration, minor discontinuities (such as fillets or asperities incident to the attachment to substrate 24) are ignored. This point is the origin 36 of the shank 28.

Though it is not necessary that a demarcation be apparent between the base 26 and the shank 28, it is also not necessary that the edges or sides of the shank 28 be contiguous with the outer edges of the base 26. The shank 28 may project from the base 26 at a point somewhat inwardly away from the outer edges of the base 26 such that the base 26 will have an annular perimeter 25 as can be seen in FIG. 1. An annular perimeter 25 is a relatively thin layer of prong material attached to the substrate 24 which forms a ring around the shank 28 at the point where the shank 28 is attached to the base 26. The annular perimeter 25 is not considered to be a fillet or asperity, but is considered to be part of the base 26 of the prong 22.

The shank 28 makes an angle $\alpha$ with the plane of the substrate 24. As used herein, the term "plane of the substrate" refers to the flat, planar surface of the substrate 24 at the base 26 of the principal prong 22 under consideration. The angle $\alpha$ is determined as follows. The prong 22 is viewed in profile. The "profile view" of the prong 22 is one of two particular side views and found as follows. The prong 22 is visually inspected from the side views such that the direction having the maximum lateral projection 38 becomes apparent. The "lateral projection" is the distance taken laterally and parallel to the plane of the substrate 24 from the center of the base 26 in such view, i.e. the origin 36 of the shank 28, to the projection of the furthest laterally remote point on the prong 22 visible in such view when such point is longitudinally and perpendicularly projected downward to the plane of the substrate 24.

Figure 2:
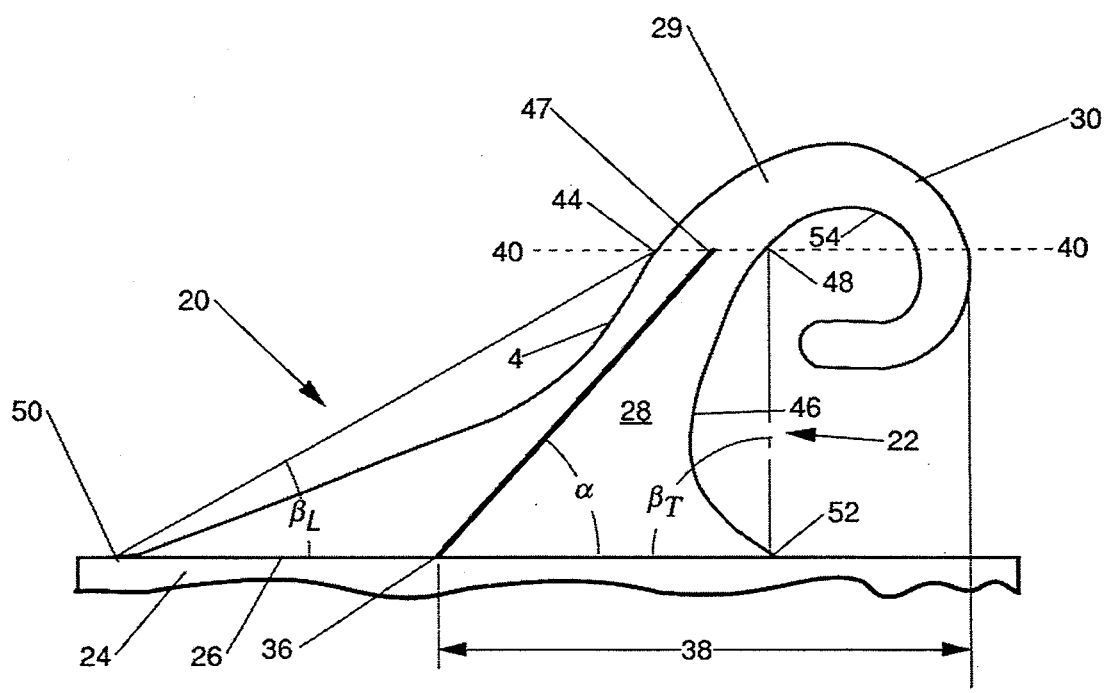
FIG. 2 is a side elevational view of one prong of the fastening system shown in FIG. 1.

It will be apparent to one skilled in the art that the maximum lateral projection 38 is that projection from the origin 36 to the outer periphery of the shank 28 or engaging means 30. The side view of the prong 22 which maximizes the lateral projection 38 is the profile view of such prong 22. It will also be apparent to one skilled in the art that if the fastening system 20 is produced by the process described and claimed below, and if the maximum lateral projection 38 is generally oriented in the machine direction, then the profile view will be generally oriented in the cross-machine direction. It will also be apparent that if the maximum lateral projection 38 is generally oriented in the cross-machine direction then the profile view will be generally oriented in the machine direction. The side elevational view shown in FIG. 2 is one of the profile views of the prong 22. It will be further apparent to one skilled in the art that there is another profile view, generally 180° opposite from the profile view shown (so that the maximum lateral projection 38 is oriented towards the left of the viewer). Either of the two profile views is generally equally well suited for the procedures and usages described hereinbelow.

The origin 36 of the shank 28 is found, as described above, with the prong 22 in the profile view. While still maintaining the prong 22 in the profile view, an imaginary cutting plane 40—40, generally parallel to the plane of the substrate 24, is then brought into tangency with the periphery of the prong 22 at the point or segment of the prong 22 having the greatest perpendicular distance from the plane of the substrate 24. This corresponds to the portion of the prong 22 having the highest elevation. The imaginary cutting plane 40—40 is then brought one-fourth of such greatest perpendicular distance closer to the substrate 24 from the point of highest elevation, so that the imaginary cutting plane 40—40 intercepts the prong 22 at a longitudinal elevation three-fourths of the perpendicular distance from the plane of the substrate 24.

The imaginary cutting plane 40—40 is then used to determine three points on the prong 22. The first point is that point where the cutting plane intercepts the leading edge 42 of the prong 22 and is referred to as the 75% leading point 44. The "leading edge" is the apex of the periphery of the shank 28 which longitudinally faces away from the plane of the substrate 24. The second point is disposed about 180° through the center of the prong 22 and is the point where the cutting plane 40—40 intercepts the trailing edge 46 of the prong 22 and is referred to as the 75% trailing point 48. The "trailing edge" is the apex of the periphery of the shank 28 which longitudinally faces towards the substrate 24 and is generally oppositely disposed from the leading edge 42. The straight line connecting these two points falls, of course, within the cutting plane 40—40 and is bisected to yield the midpoint 47 of the imaginary cutting plane 40—40. A straight line is then drawn connecting the midpoint 47 of the imaginary cutting plane 40—40 with the origin 36 of the shank 28 at the base 26. The included angle $\alpha$ this line defines relative to the plane of the substrate 24 is the angle $\alpha$ of the shank 28.

Alternatively stated, the angle $\alpha$ which the shank 28 makes relative to the plane of the substrate 24 is the 90° complement of that angle furthest from the perpendicular defined by the line, found in any side view, connecting the cutting plane midpoint 47 and the origin 36. Hence, the smallest angle relative to the plane of the substrate 24 when this line is viewed in any direction radially towards the shank 28, and particularly the origin 36, which direction is generally parallel to the plane of the substrate 24 and orthogonal to the perpendicular is the angle $\alpha$ of the shank 28. It is to be recognized that when a prong 22 having a maximum lateral projection 38 oriented in the machine direction is viewed approximately in the machine direction, or approximately 180° therefrom, or when a prong 22 having a maximum lateral projection 38 oriented in the cross-machine direction is viewed approximately in the cross-machine direction, the apparent angle $\alpha$ of the shank 28 will be about 90°. However, as discussed above, the angle $\alpha$ to be measured is that which deviates furthest from the perpendicular and, therefore, is generally that angle $\alpha$ determined when the prong 22 is viewed in profile, typically from about the cross-machine direction for a prong 22 oriented in the machine direction, and from about the machine direction for a prong 22 oriented in the cross-machine direction.

The angle $\alpha$ of the shank 28 may be generally perpendicular to the plane of the substrate 24, or is preferably oriented in an acute angular relation relative thereto to provide increased peel strength in a particular direction, which direction is generally parallel to the maximum longitudinal projection 38. However, the angle $\alpha$ of the shank 28 should not deviate excessively from the perpendicular, otherwise a fastening system 20 of more directionally specific shear strength results. For the embodiment described herein, a shank 28 having an angle $\alpha$ between about 45° and about 80°, preferably about 65°, works well. If the angle of the shank 28 is less than about 80°, the shank 28 is considered to be nonperpendicularly oriented relative to the plane of the substrate 24 (without regard to lateral orientation).

The imaginary cutting plane 40—40 and profile view can also be utilized to determine the angles of the leading edge 42 and the trailing edge 46 relative to the plane of the substrate 24. To determine these angles, the 75% leading point 44 and 75% trailing point 48 are found as described above. The base leading point 50 is found as follows. The line through the base 26 as viewed in profile is brought to intersect the leading edge 42 of the shank 28. This intersection is the "base leading point." As noted above, minor discontinuities in the shank 28 near the base 26, incident to attachment to the substrate 24, are not considered when determining the base leading point 50. The 75% leading point 44 is connected by a straight line to the base leading point 50. This straight line forms an included angle $\beta_L$ relative to the plane of the substrate 24 and opening in the direction of the origin 36 and center of the shank 28. The angle $\beta_L$ is referred to as the angle of the leading edge 42 or simply the leading edge angle.

The base trailing point 52 is generally disposed 180° from the base leading point 50, through the center of the base 26, and found as follows. The line through the footprint of the base 26 as viewed in profile is brought to intersect the trailing edge 46 of the shank 28. This intersection is the "base trailing point." As noted above, minor discontinuities in the shank 28 near the base 26, incident to attachment to the substrate 24, are not considered when determining the base trailing point 52. As described above, the 75% trailing point 48 is connected with the base trailing point 52 by a straight line. This straight line forms an included angle $\beta_T$ relative to the plane of the substrate 24 and opening in the direction of the origin 36 and center of the shank 28. The included angle $\beta_T$ is referred to as the angle of the trailing edge 46 or simply the trailing edge angle.

The leading edge 42 and trailing edge 46 included angles $\beta_L$ and $\beta_T$ define the parallelism of the sides of the shank 28. If the angles $\beta_L$ and $\beta_T$ of the leading and trailing edges 42 and 46 are not supplementary to each other (do not add to an arithmetic sum of about 180°) the sides of the shank 28 are said to be nonparallel. If the sides of the shank 28 are nonparallel, the straight lines which define the angles $\beta_L$ and $\beta_T$ (connecting the base leading and trailing points 50 and 52 with the 75% leading and trailing points 44 and 48 respectively) intersect, either above or below the plane of the substrate 24. If the angles $\beta_L$ and $\beta_T$ of the leading and trailing edges 42 and 46 are unequal and the lines defining such angles intersect above the plane of the substrate 24 (longitudinally outwardly of the base 26), the prong 22 will converge from the base 26 towards the distal end and engaging means 30. Only if the angles $\beta_L$ and $\beta_T$ of the leading and trailing edges 42 and 46 have the same sense i.e., are oriented in the same direction, and supplementary magnitudes are the angles $\beta_L$ and $\beta_T$ of the leading and trailing edges 42 and 46 determined to be equal and the sides of the shank 28 to be parallel.

A shank 28 having a leading edge 42 which forms a leading edge angle $\beta_L$ with the substrate of about 45°±30° is suitable. A trailing edge 46 which forms a trailing edge angle $\beta_T$ with the substrate of about 65°±30° is suitable. A shank 28 having these angles $\beta_L$ and $\beta_T$ of the leading and trailing edges 42 and 46 works well with the aforementioned spectrum of included angles $\alpha$ of the shank 28 to yield a tapered shank 28, advantageously oriented relative to the substrate 24 to provide high shear and peel strengths without requiring excessive prong material.

The foregoing measurements are easily made using a Model 100-00 115 goniometer sold by Rame'-Hart, Inc. of Mountain Lakes, N.J. If more precise measurement is desired, it will be recognized by one skilled in the art that determination of the profile view, origin 36, cutting plane 40—40, leading angle $\beta_L$, trailing angle $\beta_T$, base points 50 and 52, 75% points 44 and 48, and the angle $\alpha$ of the shank 28 can be advantageously performed by making a photograph of the prong 22. A model 1700 scanning electron microscope sold by Amray, Inc. of New Bedford, Mass. has been found to work well for this purpose. If necessary, several photographs may be taken to determine the maximum lateral projection 38 and hence, either profile view.

The shank 28 should longitudinally project from the base 26 a distance sufficient to space the engaging means 30 from the substrate 24 at an elevation which allows the engaging means 30 to readily intercept or engage the strands of the receiving surface. A relatively longer shank 28 provides the advantage that it can penetrate deeper into the receiving surface and thereby allow the engaging means 30 to intercept or engage a greater number of strands or fibers. Conversely, a relatively shorter shank 28 length provides the advantage that a relatively stronger prong 22 results, but also provides correspondingly less penetration into the receiving surface and may therefore be unsuitable for receiving surfaces such as wool or loosely stitched bonded materials which have less densely packed strands or fibers.

As described above, the longitudinal length of the shank 28 determines the longitudinal spacing of the engaging means 30 from the substrate 24. The "longitudinal spacing" is the least perpendicular distance from the plane of the substrate 24 to the periphery of the engaging means 30. For an engaging means 30 of constant geometry, the longitudinal spacing of the engaging means 30 from the substrate 24 becomes greater with increasing longitudinal shank 28 length. A longitudinal spacing of at least about twice the strand or fiber diameter of the intended receiving surface, and preferably about 10 times as great as such fiber or strand diameter provides good interception or engagement and retention of such strands or fibers by the engaging means 30 of the fastening system 20. For the embodiment described herein, a prong 20 having a longitudinal spacing of about 0.10 millimeters to about 0.20 millimeters (0.004 to 0.008 inches) works well.

The shape of the cross section of the shank 28 is not critical. Thus the shank 28 may be of any cross section desired, according to the aforementioned parameters relating to the cross section of the base 26. The "cross section" is the planar area of any part of the prong 22 taken perpendicular to the shank 28 or the engaging means 30. As noted above, the shank 28 is preferably tapered to decrease in cross section as the distal end of the shank 28 and engaging means 30 of the prong 22 are longitudinally and laterally approximated. This arrangement provides a corresponding decrease in the moment of inertia of the shank 28 and engaging means 30 resulting in a prong 22 of more nearly constant stress when separation forces are applied to the fastening system 20, and thereby diminishes the quantity of superfluous materials incorporated into the prong 22.

To maintain the desired geometry over a wide range of prong 22 sizes, a generally uniform ratio of cross sectional areas can be utilized to scale the prongs 22. One ratio which generally controls the overall taper of the prong 22 is the ratio of the area of the cross section of the base 26 to the area of the cross section of the prong 22, at the highest elevation of the prong 22. The phrase "highest elevation" refers to the that point or segment of the shank 28 or the engaging means 30 having the greatest perpendicular distance from the plane of the substrate 24. Typically, prongs 22 having a base 26 cross sectional area to highest elevation cross sectional area ratio in the range of about 2:1 to about 9:1 work well.

A generally circular shank 28 which tapers from a base 26 diameter, as discussed above, ranging from about 0.10 millimeters to about 0.30 millimeters (0.004 to about 0.012 inches) to a highest elevation diameter, of about 0.07 millimeters to about 0.25 millimeters (0.003 to 0.010 inches) has been found suitable for the embodiment discussed herein. Specifically, a generally circular shaped cross section of about 0.20 millimeters (0.008 inches) diameter at the highest elevation provides a cross sectional area at highest elevation of about 0.040 square millimeters (0.000064 square inches). A generally circular shaped base 26 cross section of about 0.30 millimeters (0.012 inches) provides a base 26 cross sectional area of about 0.09 square millimeters (0.00014 square inches). This structure results in a ratio of base 26 cross sectional area to highest elevation cross sectional area of about 2.25:1, which is within the aforementioned range.

The engaging means 30 is joined to the shank 28, and preferably is contiguous with the distal end of the shank 28. The engaging means 30 projects radially away and outwardly from the periphery of shank 28, and may further have a vector component which longitudinally projects, i.e. towards or away from the substrate 24. As used herein the term "engaging means" refers to any protrusion lateral to the periphery of shank 28 (other than minor asperities in the periphery of the shank 28), which protrusion resists separation or removal from a receiving surface. The term "periphery" means the outer surface of the prong 22. The term "radially" means from or towards the perpendicular to the substrate 24, which perpendicular passes through the origin 36 which is generally centered within the footprint of the base 26.

Particularly, the lateral protrusion has a vector component parallel to and facing towards the plane of the substrate 24. It is to be recognized that the engaging means 30 and shank 28 may have both lateral and longitudinal vector components. It is not important that a sharply defined terminus of the shank 28 distal end be apparent, or that a demarcation between the shank 28 and engaging means 30 be discernible at all. It is only necessary that a longitudinally oriented face of the shank 28 periphery be interrupted so that the engaging means 30 has a face with a vector component parallel to and facing the plane of the substrate 24.

The engaging means 30 may have a greater lateral projection 38 than the shank 28, or vice-versa, as desired. As illustrated in the figures, the engaging means 30 is preferably generally arcuate and may have a reentrant curve. If the engaging means 30 has a reentrant curve, the engaging means 30 includes a segment which longitudinally approximates the substrate 24 at the base 26 or a location laterally spaced from the base 26. This segment is laterally directed towards the shank 28, although the segment need not be radially directed towards the origin 36.

The engaging means 30 of each prong 22 of the fastening system 20 may laterally extend substantially in the same direction, if a relatively unidirectionally oriented peel strength is desired, or may be randomly oriented to provide substantially isotropic peel strengths in any lateral direction. The engaging means 30 may be hook-shaped tines which project substantially from one side of the shank 28, defining a generally convex outline, and penetrate the opening of the receiving surface to intercept the strands or fibers of the receiving surface at the inner radius of curvature 54 of the engaging means 30. The interference between the engaging means 30 and strands or fibers of the receiving surface prevents release of the fastening system 20 from the receiving surface until the peel strength or shear strength of the fastening system 20 is exceeded. The engaging means 30 should not radially project too far in the lateral direction, otherwise the engaging means 30 may not penetrate the opening of the receiving surface. The cross section of the engaging means 30 should be sized to penetrate the openings of the receiving surface.

The cross sectional area and geometry of the engaging means 30 are not critical, so long as the engaging means 30 has structural integrity which provides sufficient shear and bending strengths to accommodate the desired peel and shear strengths of a fastening system 20 having an array of prongs 22 of a given density. For the embodiment described herein, a hook-shaped tine engaging means 30 having a maximum lateral projection 38 from the center of the base 26 to the remote lateral periphery of about 0.18 millimeters to about 0.34 millimeters (0.007 to 0.013 inches) is suitable.

The array of prongs 22 may be of any pattern and density as desired, to achieve the peel and shear strengths required for the particular application of the fastening system 20. Generally as the array density increases, peel strength and shear strength proportionately increase in a linear fashion. The individual prongs 22 should not be so closely spaced as to interfere with and prevent the engaging means 30 of the adjacent prongs 22 from intercepting strands or fibers of the receiving surface. If the prongs 22 are too closely spaced, compacting or matting of the receiving surface strands or fibers may occur, occluding the openings between the strands or fibers. Conversely, the prongs 22 should not be so distantly spaced as to require an excessive area of substrate 24 to provide a fastening system 20 of adequate shear and peel strengths.

It is advantageous to dispose the prongs 22 in rows, so that each prong 22 is generally equally spaced from the adjacent prong 22. The rows are generally oriented in the machine direction and cross-machine direction according to the manufacturing process described and claimed below. Generally, each machine direction and cross-machine direction row of prongs 22 should be equally spaced from the adjacent machine direction and cross-machine direction rows of prongs 22, to provide a generally uniform stress field throughout the fastening system 20 and the receiving surface when separation forces are applied to the fastening system 20 and the receiving surface.

As used herein the term "pitch" refers to the distance, measured either in the machine direction or cross-machine direction, between the centers of the footprints of the bases 26 of prongs 22 in adjacent rows. Typically a fastening system 20 having an array of prongs 22 with a pitch ranging from about 1.0 millimeters to about 2.0 millimeters (0.039 to 0.078 inches) in both directions is suitable, with a pitch of about 1.3 millimeters (0.051 inches) being preferred. Adjacent cross-machine direction rows are preferably offset approximately one-half pitch in the cross-machine direction to double the distance in the machine direction between the adjacent cross-machine direction rows.

The prongs 22 may be thought of as disposed in a matrix on a one square centimeter grid having an array of prongs 22 with about 2 to about 20 rows of prongs 22 per centimeter (5 to 50 rows per inch) in both the machine and cross-machine directions.

The method of the present invention can produce a fastening system having a very dense array of prongs. This is because the density of the array of prongs of the present invention is limited only by the number of meshes or apertures that can be produced in the depositing member. Currently, it is possible to produce a depositing member having up to about 1600 meshes per square centimeter (10,000 meshes per square inch). Therefore, it is believed that a fastening system having up to about 1600 prongs per square centimeter (10,000 prongs per square inch) can be produced using the method described herein.

The prongs 22 may be made of any thermally sensitive material which is stable and shape retaining when solid, but not so brittle that failure occurs when the fastening system 20 is subjected to separation forces. As used herein, "thermally sensitive" means a material which gradually changes from the solid state to the liquid state upon the application of heat. Failure is considered to have occurred when the prong 22 has fractured or can no longer sustain a reaction in the presence of and when subjected to separation forces. Preferably the material has an elastic tensile modulus, measured according to ASTM Standard D-638, of about 24,600,000 to about 31,600,000 kilograms per square meter (35,00 to 45,000 pounds per square inch).

Further, the prong material should have a melting point low enough to provide for easy processing and a relatively high viscosity to provide a tacky and tough consistency at temperatures near the material melting point, so that the shanks 28 may be stretched and the engaging means 30 easily formed according to the method of manufacture recited below. It is also important that the prongs 22 be viscoelastic, to allow for more variation in the parameters affecting prong structure, and particularly the geometry of the engaging means 30.

The viscosity may be measured with a Rheometrics Model 800 Mechanical Spectrometer using the dynamic operating mode at a 10 Hertz sampling frequency and 10% material strain. A disk and plate type geometry is preferred, particularly with a disk having a radius of about 12.5 millimeters and a gap of about 1.0 millimeter between the disk and plate.

The prongs 22 are preferentially comprised of a thermoplastic material. The term "thermoplastic" refers to uncrosslinked polymers of a thermally sensitive material which flows under the application of heat or pressure. Hot melt adhesive thermoplastics are particularly well suited to manufacture the fastening system 20 of the present invention, particularly in accordance with the process described and claimed below. As used herein the phrase "hot melt adhesive" refers to thermoplastic compounds, normally solid at room temperature, which become fluid at elevated temperatures and which are applied in the molten state. Examples of hot melt adhesives may be found in the "Handbook Of Adhesives", Second Edition by Irving Skeist, published in 1977 by Van Nostrand Reinhold Company, 135 West 50th Street, New York, N.Y., 10020, which is incorporated herein by reference. Polyester and polyamide hot melt adhesives are suitable. As used herein, the terms "polyester" and "polyamide" mean chains having repeating ester and amide units respectively.

The viscosity and rheology characteristics of particularly preferred thermally sensitive materials are disclosed in U.S. patent application Ser. No. 07/969,604, "Method For Manufacturing A Refastenable Mechanical Fastening System and Fastening System Produced Therefrom", filed in the name of David J. K. Goulait and Dennis A Thomas on Oct. 30, 1992, which patent application is incorporated herein by reference.

SKIN-FRIENDLY MECHANICAL FASTENING SYSTEM

When a fastening system 20 having prongs 22 is used as the fastening means for a disposable diaper or incontinent brief as described more fully hereinbelow or is used on a sanitary napkin as a means for securing the sanitary napkin to the panty of the wearer, it is desirable to have a fastening system that is skin-friendly. As used herein, the term "skin-friendly" refers to a fastening system which is substantially non-irritating and non-abrasive to human skin. A particularly preferred sanitary napkin configuration is described in U.S. patent application Ser. No. 07/988,541, "Disposable Absorbent Article Having An Improved Mechanical Fastening System", filed concurrently herewith in the names of David J. K. Goulait, Dennis A. Thomas, and Maureen E. Stanley, which patent application is incorporated herein by reference.

It has been found that a more skin-friendly hook fastening material can be produced by: 1) increasing the number of prongs per unit area in an array; 2) adjusting the shape of the prong and/or the angle of the shank relative to the substrate; 3) forming the prongs on a "compressible" substrate; and/or 4) using "softer" resins to form the prongs.

It has been found that a fastening system having a dense array of prongs will tend to be more skin-friendly than a fastening system having a less dense array of prongs. Preferably, the fastening system will have prongs disposed in an array with about 8 to about 40 rows of prongs per centimeter (20 to 100 rows per inch) in each direction. This grid will result in a fastening system having about 64 to about 1600 prongs per square centimeter (400 to 10,000 prongs per square inch) of substrate 24. More preferably, the fastening system 20 will have from about 10 to about 30 rows of prongs per centimeter (25 to 75 rows per inch). This grid will result in a fastening system having from about 100 to about 900 prongs per square centimeter (625 to 5625 prongs per square inch) of substrate. Most preferably, the fastening system 20 will have from about 12 to about 24 rows of prongs per centimeter (30 to 60 rows per inch). This grid will result in a fastening system having from about 144 to about 576 prongs per square centimeter (900 to 3600 prongs per square inch) of substrate. In a preferred embodiment the fastening system will have from about 16 rows of prongs per centimeter (40 rows per inch) in each direction. This grid will result in a fastening system having from about 256 prongs per square centimeter (1600 prongs per square inch) of substrate. However, it is believed that a fastening system having 24 rows of prongs per centimeter (60 rows per inch) in each direction will produce a very skin friendly fastening system and may be even more preferred. This grid will result in a fastening system having about 576 prongs per square centimeter (3600 prongs per square inch) of substrate.

It has also been found that a more skin-friendly fastening system can be produce by using a substrate which is somewhat compressible. As used herein, the term "compressible" will refer to a substrate which will compress when pressure is applied to the prong and/or a substrate which will enable a prong to pivot or deflect when pressure is applied to the prong. An example of a compressible substrate is an foam material such as a natural foam rubber, a polyurethane foam, natural sponge, synthetic sponge, and the like.

Figure 7:
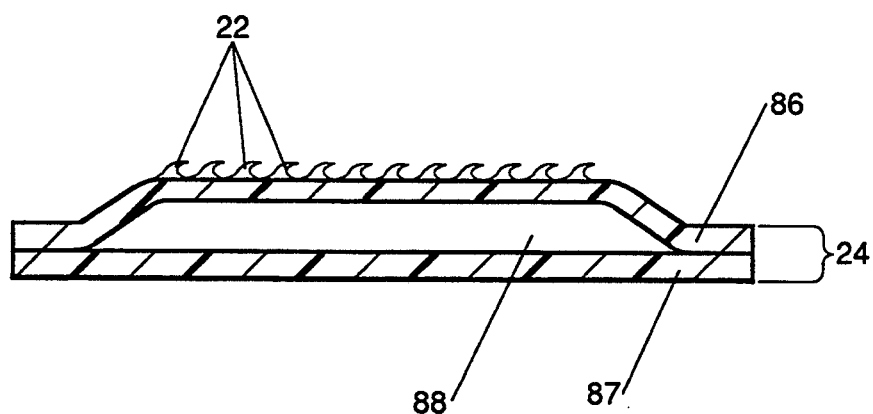
FIG. 7 is a cross sectional view of a fastening system of the present invention comprising a compressible substrate comprised of two layers of material joined at the perimeter to form a pocket.

Another example of a compressible substrate is the multilayer substrate 24 of the mechanical fastening system 54 shown in FIG. 7. The substrate 24 of FIG. 7 comprises a top layer 86, a bottom layer 87 joined to the top layer to form a pocket 88, and a fluid positioned within the pocket 88. The multilayer substrate may comprise a single pocket 88 as shown in FIG. 7 or may comprise a plurality of individual pockets. If the multilayer substrate 24 comprises a plurality of individual pockets, one or more prongs may be positioned on the top layer over each individual pocket.

The top layer 86 should be capable of being rolled, to support conventional manufacturing processes, flexible so that the substrate 24 may be bent or flexed in a desired configuration, and able to withstand the heat of the liquid prongs 22 being deposited thereon without melting or incurring deleterious effects until such prongs 22 freeze. The top layer 86 should be capable of containing the fluid without leaking and should be strong enough to hold the fluid without rupturing. Suitable materials for the top layer 86 include rubber, vinyl, films, particularly polyolefinic films and preferably polyester films. A polyester film substrate 24 having a basis weight of 17.1 grams per square meter (14.26 grams per square yard) and a thickness of about 0.008 to about 0.15 millimeters (0.0003 to 0.006 inches) is suitable. Such materials are commercially available from Hoechst Celanese of Greer, S.C., 29651 and sold under the trade name Hostaphan 2400 polyester film.

The bottom layer 87 should also be capable of being rolled to support conventional manufacturing processes, flexible so that the substrate 24 may be bent or flexed in a desired configuration, non-porous enough to contain the fluid without leaking, and strong enough to hold the fluid without rupturing. Suitable materials for the bottom layer 87 may be the same materials disclosed for use as the top layer 86. The bottom layer 87 may be joined to the top layer 86 by any means well known in the art such as adhesive bonding, heat sealing, ultrasonic bonding, autogenous bonding, and the like. A particularly preferred method of autogenously bonding the top layer 86 and bottom layer 87 together is disclosed in U.S. Pat. No. 4,854,984, issued Aug. 8, 1989 to Ball et al., which patent is incorporated herein by reference.

The fluid may be any liquid or gas which is able to dissipate from one area of the substrate 24 when pressure is applied to that area and return to that area when the pressure is removed. Examples of suitable fluids for use with the substrate shown in FIG. 7 include water, air, inert gas, and the like. For reasons of simplicity and economics the fluid is preferably the ambient atmosphere present at the point of manufacture of the multilayer substrate. The prongs 22 may be printed or otherwise formed on the top layer 86 after the pocket 88 has been formed and the fluid has been trapped in the pocket 88 or inserted therein. However, it is preferred that the prongs 22 be printed or otherwise formed on the top layer 86 before the pocket 88 has been formed. In a preferred embodiment the prongs 22 will be formed on the top layer 86 prior to joining the top layer 86 to the bottom layer 87.

It has also been found that a more skin-friendly fastening system can also be produced by using "soft" resins. As used herein the term "soft resin" shall refer to a resin capable of forming engaging elements which are flexible or capable of bending under a force without rupturing. It has been found that ethylene vinyl acetate based polymers (or simply "EVA resins") and polyethylene based polymers will form prongs which are very flexible and capable of bending under a force without rupturing. EVA resins and polyethylene based polymers are considered to be soft resins.

Associated with each prong 22 is a longitudinal axis 32. As used herein, the term "longitudinal axis" refers to an imaginary line generally centered at the footprint of the base 26 and laterally and longitudinally projecting through the distal end of the shank 28 to the tip 34 of the engaging means 30. The prong base 26, shank 28 and engaging means 30 are generally concentric with the longitudinal axis 32 if the prong 22 cross section is of a regular shape. If the cross section of the prong 22 is irregularly shaped, the longitudinal axis 32 is disposed at the centroid of any cross section. The "origin" of the longitudinal axis is the same as the origin of the shank, and is found as described hereinbefore.

The engaging means 30 forms an included angle $\theta$ relative to the plane of the substrate 24. It has been found that a more skin-friendly fastening system can be produced by forming prongs 22 having an engaging means 30 which forms and included angle $\theta$ of between about 90° and about 160°. As used herein, the term "included angle $\theta$" refers to the angular deviation between the extension of the perpendicular 84 to the plane of the substrate 24 (or simply "the perpendicular-to-the-plane 84") which passes through the origin 36 of base 26 and the projection of the longitudinal axis 32 (or simply "the projection 85") through the tip 34 of the engaging means 30, as seen when the prong 22 is viewed in profile. The phrase "projection of the longitudinal axis" refers to the imaginary continuation of the longitudinal axis 32 in a straight line through the tip 34 of the engaging means 30 if such axis were continued at the angle present at the tip 34 of the engaging means 30.

It is to be recognized that as the included angle $\theta$ of the engaging means 30 increases, i.e. departs further from the perpendicular-to-the-plane 84, it will become increasingly difficult for the engaging means 30 to intercept the strands or fibers of the receiving surface. However, for skin friendly fastening systems, the engaging means 30 preferably has an included angle $\theta$ of between about 90° to about 160°. More preferably, the included angle $\theta$ is between about 100° to about 150°, and most preferably is between about 110° to about 140°. However, a prong 22 having an included angle $\theta$ greater than about 160° or less than 90° may also be used though such a prong will tend to be less skin friendly.

Figure 8:
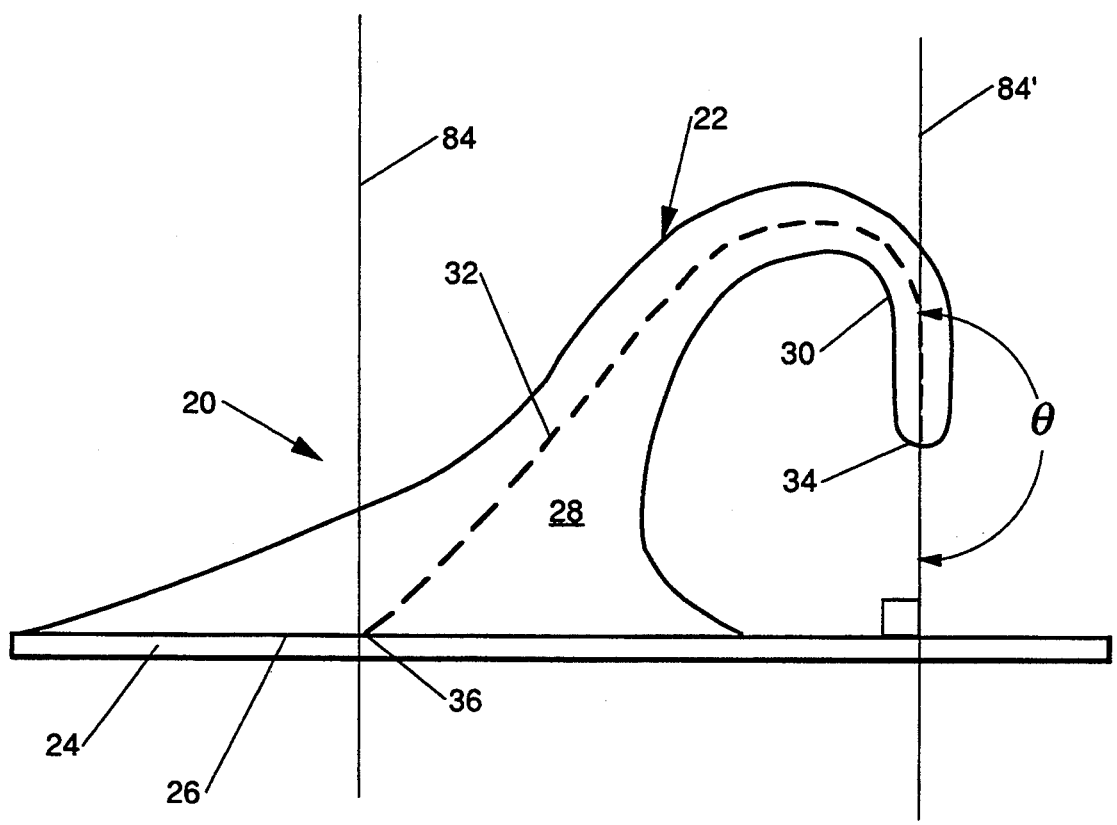
FIG. 8 is a side elevational view of one prong of a fastening system of the present invention having an included angle $\theta$ of about 180° relative to a line drawn parallel to the extension of the perpendicular to the substrate.
Figure 9:
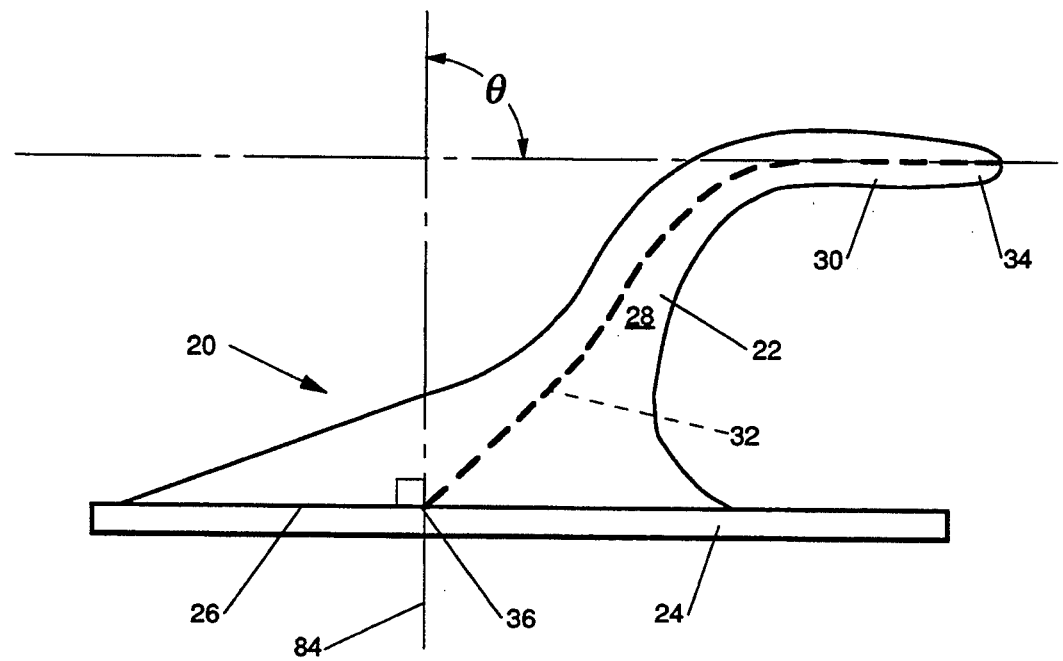
FIG. 9 is a side elevational view of one prong of a fastening system of the present invention having an included angle $\theta$ of about 90° relative to the extension of the perpendicular to the substrate.
Figure 10:
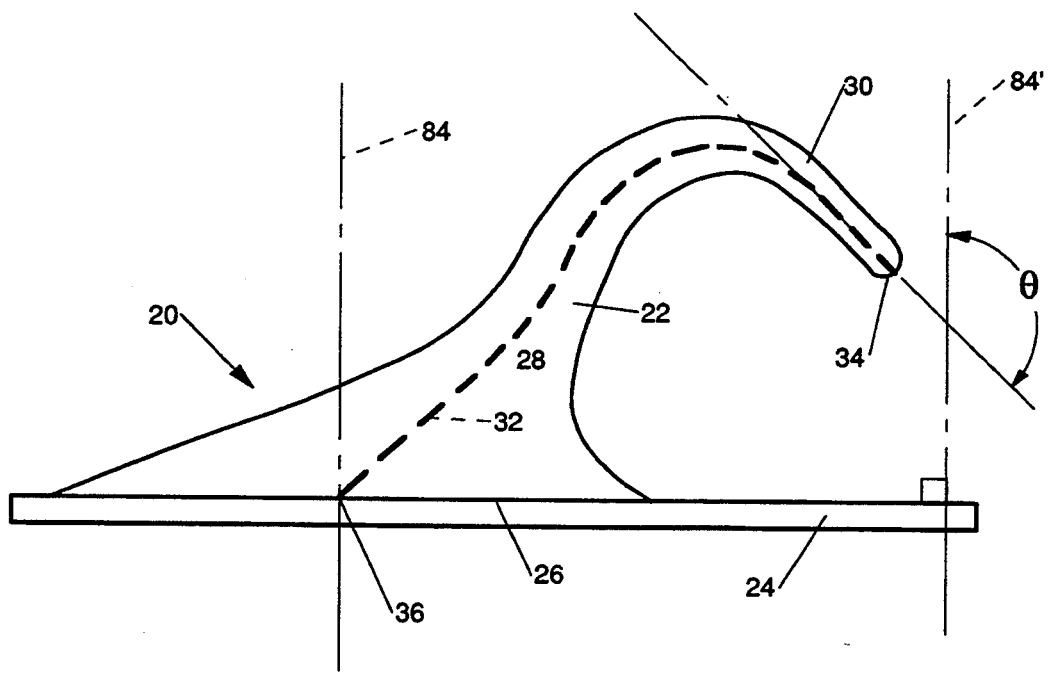
FIG. 10 is a side elevational view of one prong of a fastening system of the present invention having an included angle $\theta$ of about 140° relative to the extension of the perpendicular to the substrate.

Referring to FIG. 8, there is shown a prong 22 having an included angle $\theta$ of about 180°. Although the included angle $\theta$ is generally taken relative to the perpendicular-to-the-plane 84 which passes through the origin 36, for simplicity the included angle $\theta$ of the prong 22 of FIG. 8 is taken relative to a line 84' which is drawn parallel to the perpendicular-to-the-plane 84. This is because the perpendicular-to-the-plane 84 and the projection 85 will never intersect if the included angle $\theta$ is exactly 180°. There is shown in FIG. 9 a prong 22 having an included angle $\theta$ of about 90°. There is shown in FIG. 10 a prong 22 having an included angle $\theta$ of about 140°. For simplicity the included angle $\theta$ of the prong 22 of FIG. 10 is also taken relative to a line 84' which is drawn parallel to the perpendicular-to-the-plane 84.

Such prongs 22 may be produced by any suitable method. Preferably, the prongs 22 are produced by methods which yield free formed prongs. Methods and apparatus for making such prongs 22 are more fully detailed in U.S. Pat. No. 5,058,247, issued Oct. 22, 1991 to Dennis A. Thomas and Ted L. Blaney and U.S. Pat. No. 5,116,563, issued May 26, 1992 to Dennis A. Thomas and David J. K. Goulait, which patents are incorporated herein by reference.

Figure 3:
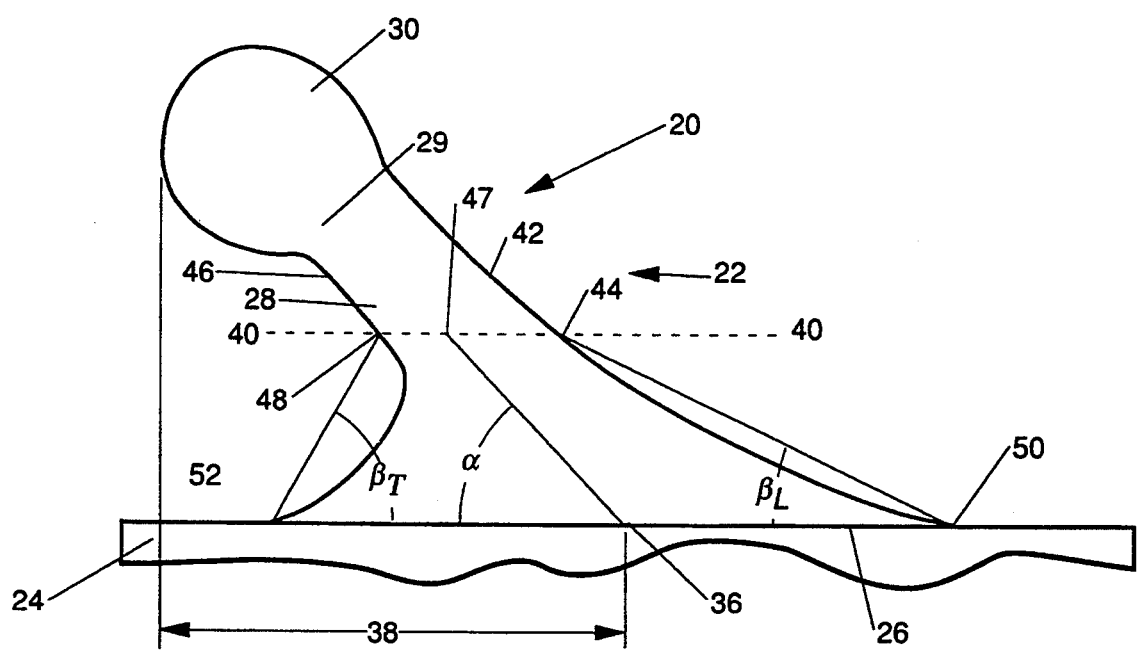
FIG. 3 is a side elevational view of a fastening system of the present invention comprising mushroom shaped prongs.

FIG. 3 shows an alternative prong configuration suitable for the skin friendly fastening system of the present invention. The prong comprises an engaging means somewhat spherical in shape. Such prongs and methods of making such prongs are described in greater detail in U.S. patent application Ser. No. 07/719,211, "Method For Manufacturing A Refastenable Mechanical Fastening System Having Azimuthally Angled Prongs And Fastening System Produced Therefrom", filed Jun. 21, 1991 in the names of Dennis A. Thomas and David J. K. Goulait; U.S. patent application Ser. No. 07/718,727, "Screen Printing Method For Manufacturing A Refastenable Mechanical Fastening System And Fastening System Produced Therefrom", filed Jun. 21, 1991 in the names of Dennis A. Thomas and David J. K. Goulait; and allowed U.S. patent application Ser. No. 07/632,283, "A Process For Manufacturing A Refastenable Mechanical Fastening System", filed Dec. 21, 1990 in the names of Dennis A. Thomas, David J. K. Goulait, and Robert G. Cox, Jr.; which patent applications are incorporated herein by reference.

PROCESS OF MANUFACTURE

FIG. 4 is a side elevational, schematic view of a particularly preferred apparatus used to produce prongs of the present invention. FIG. 4 shows a backing roll 74 and print cylinder 73 which form a nip 70 through which the substrate 24 passes. As the print cylinder 73 and backing roll 74 rotate about their axes, the molten prong material is extruded through the apertures of the print cylinder 73 onto the moving substrate 24, is stretched in a direction having a vector component parallel to the plane of the substrate 24 and is severed by the means for severing 78 to produce prongs having a distal end 29 and engaging means 30 thereon. As used herein the term "extrude" refers to forcing a substance through an opening causing the substance to be shaped, at least partially, by the opening.

the prong material is too low, the prong material may not transfer from the pressure bar to the doctor blade assembly 83 or print cylinder 73 or, subsequently, may not properly transfer from the print cylinder 73 to the substrate 24 in the desired array or pattern.

The print cylinder 73 is preferably heated to prevent solidification of the prongs 22 during transfer from the heated pressure bar 81 through the deposition on the substrate 24. Generally a print cylinder 73 surface temperature near the source material temperature is desired. A print cylinder 73 temperature of about 178° C. has been found to work well with the polyester hot melt adhesive marketed by the Bostik Company of Middletown, Mass. as No. 7199. But, the operating temperature of the print cylinder 73 may vary according to the particular prong material being used. There are many methods which can be used to heat the print cylinder 73, which will be readily apparent to one skilled in the art. A particularly preferred method of heating the print cylinder 73 is by using an infrared heater 72.

It is to be recognized that a chill roll may be necessary if the substrate 24 is adversely affected by the heat transferred from the prong material. If a chill roll is desired, it may be incorporated into the backing roll 74 using means well known to one skilled in the art. This arrangement is often necessary if a polypropylene, polyethylene or other polyolefinic substrate 24 is used.

After being deposited onto the substrate 24, the prongs 22 are severed from the the depositing member by a severing means. The prongs 22 are severed to form the engaging means 30 of the fastening system 20 and a moil. As used herein the term "moil" refers to any material severed from the prong 22 and which does not form part of the fastening system 20.

The severing means 78 should be adjustable to accommodate various sizes of prongs 22 and lateral projections 38 of engaging means 30 and also provide uniformity throughout the cross-machine direction of the array. The term "severing means" refers to anything which longitudinally separates the moil from the fastening system 20. The term "sever" refers to the act of dividing the moil from the fastening system 20 as described above. The severing means 78 should also be clean and should not rust, oxidize or impart corrodents and contaminates (such as moil material) to the prongs 22. A suitable severing means is a wire 78 disposed generally parallel to the axis of the cylinder 73 and roll 74 and spaced from the substrate 24 a distance which is somewhat greater than the perpendicular distance from the highest elevation of the solidified prong 22 to the substrate 24.

Preferably the wire 78 is electrically heated to prevent build-up of the molten prong material on the severing means 78, accommodate any cooling of the prongs 22 which occurs between the time the prong material leaves the heated pressure bar and severing occurs and to promote lateral stretching of the engaging means 30. The heating of the severing means 78 should also provide for uniform temperature distribution in the cross-machine direction, so that an array of prongs 22 having substantially uniform geometry is produced.

Generally, as the prong material temperature increases a relatively cooler hot wire 78 temperature severing means can be accommodated. Also, as the speed of the substrate 24 is decreased, less frequent cooling of the hot wire 78 occurs as each prong 22 and moil are severed, making a relatively lower wattage hot wire 78 more feasible at the same temperatures. It should be recognized that as the temperature of the hot wire 78 is increased a prong 22 having a generally shorter shank 28 length will result. Conversely, the shank 28 length and lateral length of the engaging means 30 will be increased in inverse proportion as the temperature of the hot wire 78 is decreased. It is not necessary that the severing means 78 actually contact the prong 22 for severing to occur. The prong 22 may be severed by the radiant heat emitted from the severing means 78.

For the embodiment described herein a round cross section nickel-chromium wire 78, having a diameter of about 0.64 millimeters (0.025 inches) heated to a temperature of about 343° C. to about 440° C. has been found suitable. It will be apparent that a knife, laser cutting or other severing means 78 may be substituted for the hot wire 78 described above.

It is important that the severing means 78 be disposed at a position which allows stretching of the prong material to occur prior to the prong 22 being severed from the moil. If the severing means 78 is disposed too far from the plane of the substrate 24, the prong material will pass underneath the severing means 78 and not be intercepted by it, forming a very long engaging means 30 which will not be properly spaced from the substrate 24 or adjacent prongs 22. Conversely, if the severing means 78 is disposed too close to the plane of the substrate 24, the severing means 78 will truncate the shank 28 and an engaging means 30 may not be formed.

A hot wire severing means 78 disposed approximately 3.2 millimeters to 8.3 millimeters (0.125 to 0.325 inches), preferably about 5.7 millimeters (0.225 inches) in the machine direction from the nip point 70, approximately 1.4 millimeters to 6.5 millimeters (0.056 to 0.256 inches), preferably about 4.0 millimeters (0.156 inches) radially outward from the backing roll 74 and approximately 13.7 millimeters to approximately 18.6 millimeters (0.534 to 0.734 inches), preferably about 16.1 millimeters (0.634 inches) radially outwardly from the print cylinder 73 is adequately positioned for the process of manufacture disclosed herein.

In operation, the substrate 24 is transported in a first direction relative to the depositing member. More particularly, the substrate 24 is transported through the nip 70, preferentially drawn by a take-up roll (not shown). This provides a clean area of substrate 24 for continuous deposition of prongs 22 and removes the portions of the substrate 24 having prongs 22 deposited thereon. The direction generally parallel to the principal direction of transport of the substrate 24 as it passes through the nip 70 is referred to as the "machine direction." The machine direction, as indicated by the arrow 75 of FIG. 4, is generally orthogonal the centerline of the print cylinder 73 and backing roll 74. The direction generally orthogonal to the machine direction and parallel to the plane of the substrate 24 is referred to as the "cross-machine direction."

The substrate 24 may be drawn through the nip 70 at a speed approximately 0% to approximately 10% greater than the surface speed of the cylinder 73 and roll 74. This is done to minimize bunching or puckering of the substrate 24 near the means for severing 78 the prongs 22 from the means for depositing the prong material on the substrate 24. The substrate 24 is transported through the nip 70 in the first direction at about 3 to about 31 meters per minute (10 to 100 feet per minute).

The print cylinder 73 is an example of a particularly preferred depositing member which may be used with the method of the present invention. The depositing member should be made of metal or any other suitable material which can accommodate the temperatures of the molten prong material, provide substantially uniform pitch between the prongs 22 in both the machine direction and cross-machine direction, and yield the desired density of prongs 22 within the array.

As used herein the phrase "depositing member" refers to anything through which liquid prong material is extruded in dosages corresponding to individual prongs 22. The depositing member will generally be a smooth and relatively thin piece of metal or other material having perforations or apertures through which the molten prong material is extruded onto the substrate. The depositing member may be a flat bed screen, a belt screen (such as a continuous band, belt, or conveyor having apertures) or a rotary screen, such as the screens used in the screen printing art. The depositing member, however, may also be in the form of a porous or sintered roll having an internal reservoir continuously pressure fed with molten prong material which is then extruded through the pores of the roll onto the moving substrate. As used herein the term "deposit" means to transfer prong material from the bulk form and dose such material onto the substrate 24 in units corresponding to individual prongs 22.

Preferably, the depositing member will be a rotary screen or print cylinder. A particularly preferred print cylinder 73 will be a metal cylinder, preferably constructed of nickel, having apertures 56 produced by any means well known in the art and preferably produced by means of photoengraving. Preferably a circular frame will be mounted on each end of the cylinder, which will provide the screen with structural support, maintain the screen's cylindrical shape, and will also provide a means of holding the screen in position and rotating the screen about its axis without interfering with the heated pressure bar 81 or heated hose (not shown). For convenience of description, the depositing member of the present invention shall be described as a print cylinder 73. It is to be understood, however, that the present invention applies to any method of extruding molten prong material onto a substrate to produce a fastening system having free-formed prongs.

The print cylinder 73 and backing roll 74 may be driven by any means well known in the art such as an external motive force (not shown), or the backing roll 74 may be driven by an external motive force and the print cylinder 73 driven by frictional engagement with the backing roll 74, or vice-versa.

Rotary screen printing apparatus which can be modified for use with the method of the present invention are commercially available from Graco/LTI Corporation, P.O. Box 1828, Monteray, Calif. 93940, such as the Graco/LTI Micro-Print hot melt adhesive applicator.

The size, shape and pattern of the apertures in the print cylinder 73 may vary according to the size and shape of the prongs and the density of prongs in the array that is required for the particular fastening system desired. The cross sectional area of the aperture 56, taken at the outer surface of the print cylinder 73, generally corresponds with the shape of the footprint of the base 26 of the prong 22. The cross section of the aperture 56 should be approximately equal to the desired cross section of the base 26.

For the embodiment described herein, a generally cylindrically shaped aperture 56 is adequate. Though if desired, the aperture 56 may be somewhat frustoconically tapered in shape, having a larger cross section either at the outer surface of the cylinder 73 or inner surface of the cylinder 73. For the embodiment described herein an aperture 56 having a diameter of about 0.30 millimeters to about 0.70 millimeters (0.012 to 0.028 inches) produces a suitable prong 22.

There are different methods and apparatus that are suitable to supply molten prong material to the print cylinder 73 and which are well known in the art. One suitable apparatus is disclosed is U.S. Pat. No. 4,876,982, issued Oct. 31, 1989 to Claassen, which is incorporated herein by reference. Another particularly preferred apparatus is a heated pressure bar 81 shown in FIG. 10. The heated pressure bar 81 is disposed within the print cylinder 73 and is substantially parallel to the print cylinder 73. The heated pressure bar 81 has an internal reservoir (not shown) which is fed with liquid prong material and one or more discharge ports (not shown) from which the liquid prong material uniformly flows to the inside surface of the print cylinder 73. Attached to the heated pressure bar 81 is a doctor blade assembly 83. As the print cylinder 73 rotates the doctor blade assembly 83 squeegees the molten prong material along the inner surface of the print cylinder 73 and forces the liquid prong material into the apertures 56. The doctor blade assembly 83 not only serves to force the molten prong material through the apertures 56, but also provides support to the print cylinder 73 at the point of the nip 70 to prevent the print cylinder 73 from buckling or deforming as it is pressed against the backing roll 74. The backing roll 74 may be constructed of metal or any other suitable material. A backing roll 74 having a rubber coating with a Shore A durometer hardness of about 40 to about 60 may also be used. Preferably, the doctor blade assembly 83 is pressed against the print cylinder 73 with a force of about 80 pounds per square inch as the substrate 24 passes through the nip 70. A suitable heated pressure bar 81 and doctor blade assembly 83 are commercially available from Graco/LTI Corporation, P.O. Box 1828, Monteray, Calif. 93940.

The internal reservoir of the heated pressure bar 81 should have a steady supply of thermally sensitive material. This may be provided by any means well known in the screen printing or hot melt adhesives art, but a particularly preferred method of supplying the heated pressure bar comprises a heated hose assembly (not shown), a heated tank (not shown), and a gear pump (not shown). The gear pump may be driven by a variable speed DC motor (not shown) and should provide constant uniform output at the discharge port of the heated pressure bar 81 at all line speeds. The heated tank, heated hose assembly, and heated pressure bar 81 should keep the molten prong material at the desired operating temperature. Typically, a temperature slightly above the melting point of the material is desired. The material is considered to be at or above the "melting point" if the material is partially or wholly in the liquid state. If the prong material is kept at too high a temperature, the prong material may not be viscous enough and may produce engaging means 30 which laterally connect to the prongs 22 adjacent in the machine direction. If the prong material temperature is very hot, the prong 22 will flow into a small, some-what semispherically shaped puddle and an engaging means 30 will not be formed . Conversely, if the temperature of The angle of the shank 28 can be influenced by the rate of transport of the substrate 24 past the nip 70. If prongs 22 having a shank angle α more nearly perpendicular to the substrate 24 is desired, a slower rate of transport of the substrate 24 in the first direction is selected. Conversely, if the rate of transport is increased, the angle α of the shank 28 decreases and an engaging means 30 have a greater lateral projection 38 will result.

If desired, the substrate 24 may be inclined at an angle γ, approximately 35° to approximately 55°, preferably about 45°, from the plane of the nip 70 towards the backing roll 74 to utilize the viscoelastic nature of the prong material and properly orient the engaging means 30 in the lateral direction, as well as longitudinal direction. This arrangement also provides a greater force to extract the prong material from the apertures 56 and to pull the prong 22 away from the print cylinder 73. The angle γ from the plane of the nip 70 should be increased as a lesser angle α of the shank 28 is desired. Also, increasing the angle γ of deviation from the plane of the nip 70 has a weak, but positive effect to produce engaging means 30 having a greater lateral projection 38.

After depositing prong material from the apertures 56 onto the substrate 24, the cylinder 73 and roll 74 continue rotation, in the directions indicated by the arrows 75 of FIG. 4. This results in a period of relative displacement between the transported substrate 24 and the apertures 56 during which period (prior to severing) the prong material bridges the substrate 24 and print cylinder 73. As relative displacement continues, the prong material is stretched until severing occurs and the prong 22 separated from the aperture 56 of the print cylinder 73. As used herein the term "stretch" means to increase in linear dimension, at least a portion of which increase becomes substantially permanent for the life of the fastening system 20.

As discussed above, it is also necessary to sever the individual prongs 22 from the print cylinder 73 as part of the process which forms the engaging means 30. When severed, a prong 22 is longitudinally divided into two parts, a distal end 29 and engaging means 30 which remain with the fastening system 20 and a moil (not shown) which remains with the print cylinder 73 and may be recycled, as desired. After the prongs 22 are severed from the moil, the fastening system 20 is allowed to freeze prior to contact of the prongs 22 with other objects. After solidification of the prongs 22, the substrate 24 may be wound into a roll for storage as desired.

A non-limiting illustration of the method of the present invention shows the prong material to be disposed in a heated trough (not shown) and supplied to the heated pressure bar 81 by a heated hose assembly (not shown). If a polyester resin hot melt adhesive is selected, a material temperature of approximately 177–193 degrees Celsius, preferably about 186 degrees Celsius, has been found suitable. If a polyamide resin is selected, a material temperature of approximately 193–213 degrees Celsius, preferably about 200 degrees Celsius, has been found suitable. A polyester film substrate 24 about 0.008 to about 0.15 millimeters (0.003 to 0.006 inches) in thickness works well with hot melt adhesive prongs 22.

For the illustrated operation described herein, print cylinder 73 having an array of about 15 apertures per centimeter (40 apertures per inch) in both the machine direction and cross machine direction, yielding a grid of about 237 apertures per square centimeter (1600 apertures per square inch), is suitable. This grid density may be advantageously used with a print cylinder 73 having a wall thickness of about 0.16 millimeters (0.004 inches) and a diameter of about 20.3 centimeters (8.0 inches), with apertures 56 having a diameter of 0.30 millimeter (0.012 inches). A backing roll 74 having a diameter of about 20.3 centimeters (8.0 inches) and vertically registered has been found to work well with the aforementioned print cylinder 73. The rate of transport of the substrate 24 is about 10.7 meters per minute (35 feet per minute).

A nickel-chromium hot wire 78 having a diameter of about 0.6 millimeters (0.025 inches) disposed approximately 5.7 millimeters (0.225 inches) from the nip point 70 in the machine direction, approximately 16.1 millimeters (0.634 inches) radially outward from the print cylinder 73 and approximately 4.0 millimeters (0.156 inches) from the backing roll 74 is heated to a temperature of about 430 degrees Celsius. The fastening system 20 produced by this operation is substantially similar to that illustrated by FIG. 1, which fastening system 20 may be advantageously incorporated into the illustrative article of use discussed below.

Without being bound by any particular theory, it is believed that the geometry of the engaging means 30 is governed by the elastic properties of the hot melt adhesive used to make the prong 22 and the difference in the temperature between the trailing edge 46 and the leading edge 42 of the prong 22. The trailing edge 46 of the prong 22 is shielded and insulated from the heat originating from the severing means 78. Conversely, the leading edge 42 is directly exposed to the heat of the severing means 78, which causes the leading edge 42 to solidify or freeze after the trailing edge 46. This causes elongation of the leading edge 42 and contraction of the trailing edge 46, relative to each other. As this temperature difference is increased, a relatively longer engaging means 30 is formed.

It is frequently desirable to have a fastening system 20 of the present invention with the maximum lateral projection 38 of the prongs 22 oriented in a direction other than the machine direction. For example, when using the present invention as the fastening means of a disposable diaper, it is desirable that the maximum lateral projection 38 of the prongs 22 be oriented in a direction substantially perpendicular to the direction of travel of the disposable diaper on the manufacturing line. A diaper manufacturing line requires complex and expensive machinery to cut, reorient and apply the fastening system 20 if the maximum lateral projection 38 of the prongs 22 are oriented in the machine direction. A fastening system 20 of the present invention produced with the maximum lateral projection 38 of the prongs 22 oriented in the cross-machine direction, however, would not require re-orientation before being applied to a disposable diaper. It is therefore very advantageous to be able to manufacture the fastening system 20 of the present invention with the maximum lateral projection 38 of the prongs 22 oriented in a direction other than the machine direction.

There are two angles which are made by the shank 28 of prongs 22 produced by this process. The shank 28 makes an angle α with the plane of the substrate 24 as discussed hereinbefore, and the shank 28 also makes an azimuthal angle relative to the machine direction of the substrate 24. As used herein, the term "azimuthal angle" refers to the angle the maximum lateral projection 38 makes relative to the machine direction of the substrate when viewed from above. As used herein "viewed from above" refers to viewing the prongs 22 from a direction which is perpendicular to the plane of the substrate 24. The term "machine direction" refers to the direction generally parallel to the principle direction of transport of the substrate 24 as it passes through the nip.

Methods of forming azimuthally angled, free formed prongs are discussed in greater detail in commonly assigned, co-pending patent application Ser. No. 07/632,283, "Process Of Manufacturing A Refastenable Mechanical Fastening System", filed Dec. 21, 1990, in the name of D. A. Thomas, D. J. K. Goulait and R. G. Cox, Jr., allowed Jul. 31, 1992, and commonly assigned, co-pending patent application Ser. No. 07/719,211, "Method for Manufacturing a Refastenable Mechanical Fastening System Having Azimuthally Angled Prongs and Fastening System Produced Therefrom", filed Jun. 21, 1991, in the name of D. A. Thomas and D. J. K. Goulait, which patent applications are incorporated herein by reference.

The prongs 22 may also be made according to a modified gravure printing process. The method comprises the steps of depositing the molten thermally sensitive material onto the substrate from the cells of a depositing member, such as a gravure printing roll, stretching the discrete amounts of molten thermally sensitive material in a direction having a vector component parallel to the plane of the substrate so as to form a prong, and solidifying the molten thermally sensitive material of the prong. A more detailed description of this method is disclosed in U.S. patent application Ser. No. 07/668,817, "Refastenable Mechanical Fastening System And Process For Manufacture Therefor", filed Mar. 7, 1991 in the name of Dennis A. Thomas (a Rule 62 Continuation Patent Application of U.S. patent application Ser. No. 07/305,354 filed Jan. 31, 1989); U.S. Pat. No. 5,058,247, issued to Dennis A. Thomas and Ted L. Blaney on Oct. 22, 1991; and U.S. Pat. No. 5,116,563, issued to Dennis A. Thomas and David J. K. Goulait on May 26, 1992; which patent applications and patents are incorporated herein by reference.

It will be further apparent to one skilled in the art that other variations are feasible. For example, a prong 22 having an engaging means 30 protruding in more than one direction may be produced. If desired, only the print cylinder 73 may be utilized in the manufacturing process, providing the substrate 24 contacts the print cylinder 73 at the point on the outer surface of the print cylinder 73 that corresponds with the point at which the doctor blade assembly 83 contacts the inner surface of the print cylinder 73.

ILLUSTRATIVE ARTICLE OF USE

Figure 5:
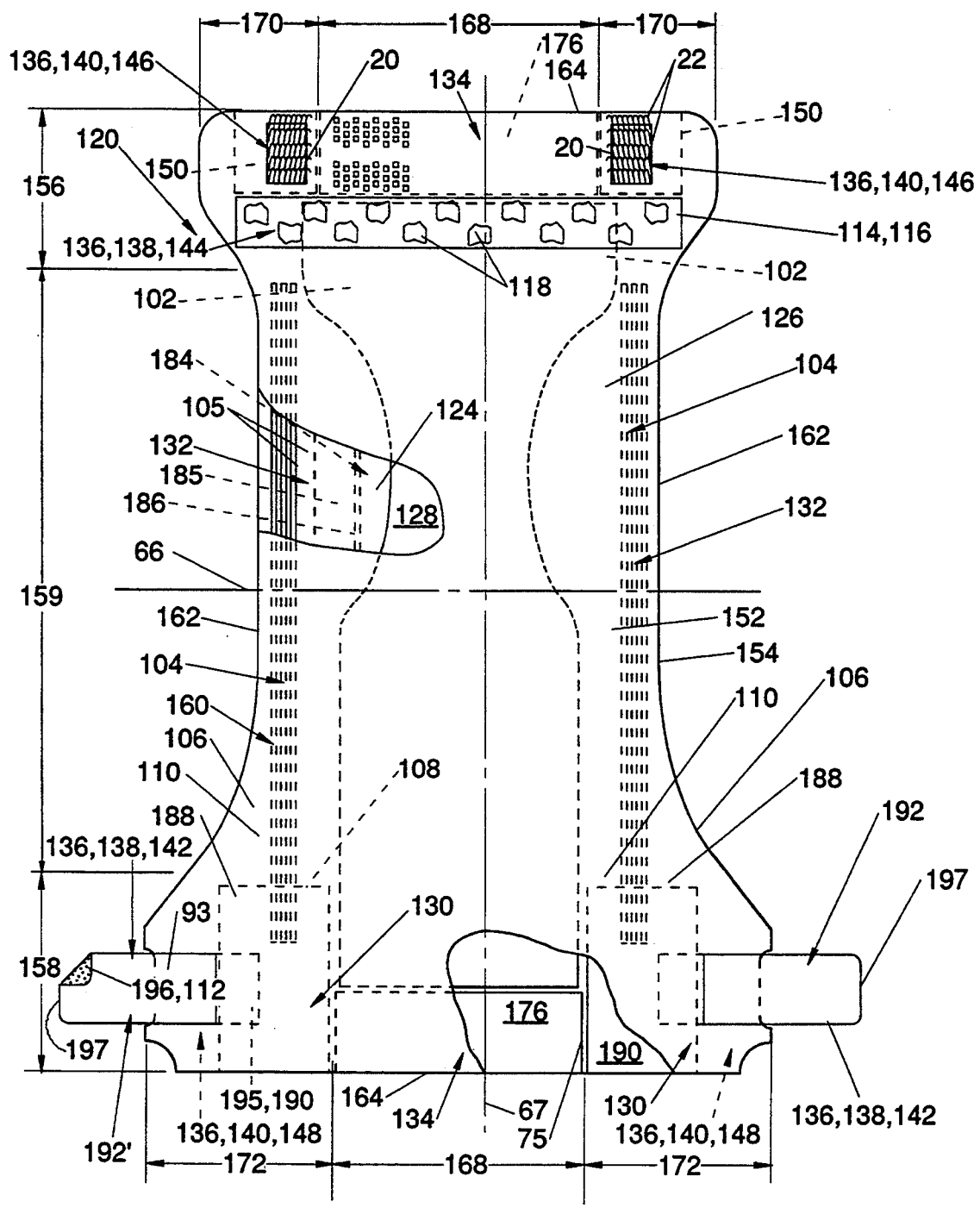
FIG. 5 is a plan view of a disposable diaper embodiment of the present invention having portions cut-away to reveal underlying structure, the outer surface of the diaper facing the viewer.
Figure 6:
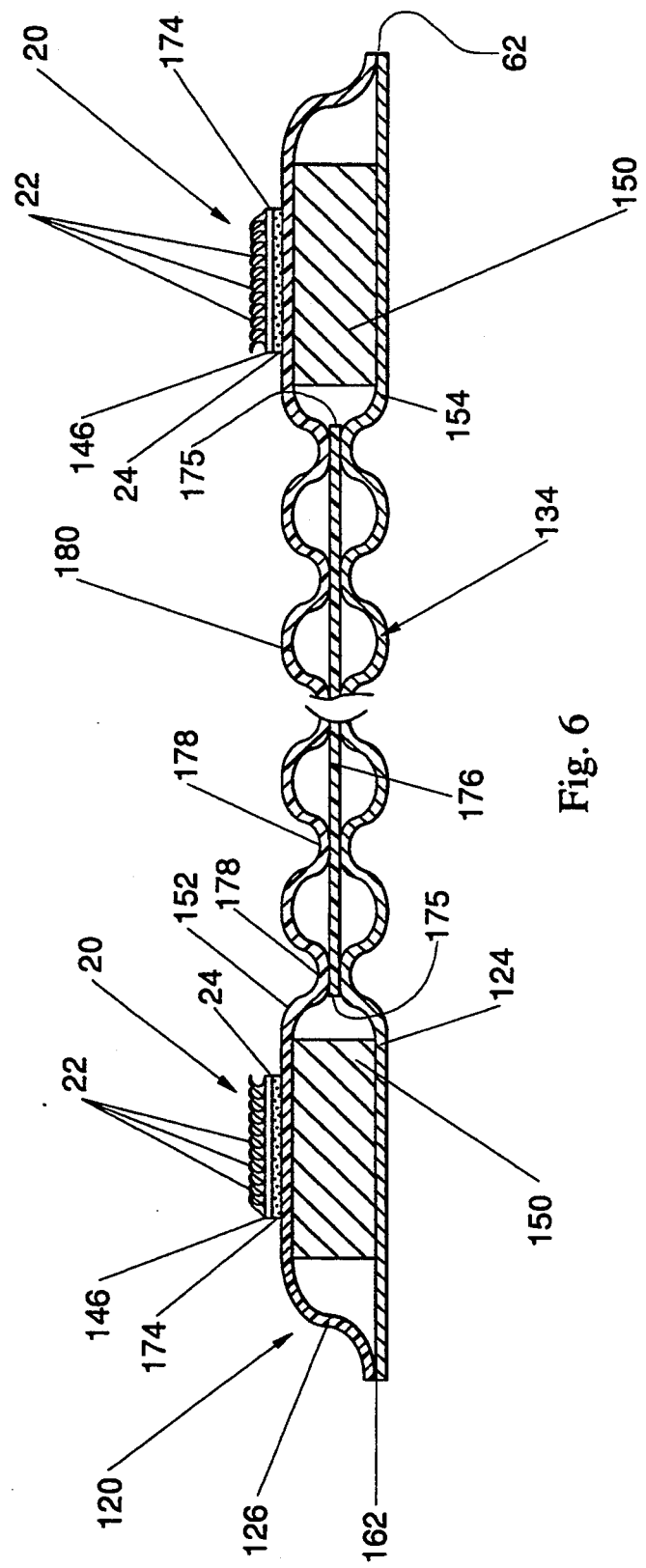
FIG. 6 is a fragmentary sectional view of the disposable diaper shown in FIG. 1 taken along section line 6—6 of FIG. 5.

An illustrative and nonlimiting example of the usage of the fastening system of the present invention in an article of manufacture follows and is illustrated in FIGS. 5 and 6. Mechanical fastening systems have been advantageously used in disposable absorbent articles as disclosed in U.S. Pat. No. 4,846,815 entitled "Disposable Diaper Having an Improved Fastening Device" issued to Scripps, on Jul. 11, 1989, which patent is incorporated herein by reference for the purpose of showing a diaper structure and the advantageous utilization of mechanical fastening systems 20 in such diaper structures.

It is known, for example, that mechanical fastening systems are less easily contaminated by oils and powders than are adhesive tape fastening systems and, further, may be easily reused. All of these features provide advantages when applied to a disposable diaper 120 intended for use on an infant. Also, a refastenable fastening system provides the advantage that the infant may be checked to see if soiling of the disposable diaper 120 has occurred during the wearing period.

As used herein, the term "absorbent article" refers to devices which absorb and contain body exudates, and, more specifically, refers to devices, such as sanitary napkins, disposable diapers, incontinent garments, and the like, which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 120, shown in FIG. 5. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, and the like.

FIG. 5 is a plan view of the diaper 120 of the present invention in its flat-out, uncontracted state (i.e., with elastic induced contraction pulled out) with portions of the structure being cut-away to more clearly show the construction of the diaper 120 and with the portion of the diaper 120 which faces the wearer, the inner surface 154, facing the viewer. As shown in FIG. 5, the diaper 120 preferably comprises a liquid pervious topsheet 124; a liquid impervious backsheet 126 joined with the topsheet 124; an absorbent core 128 positioned between the topsheet 124 and the backsheet 126; elasticized side panels 130; elasticized leg cuffs 132; an elastic waist feature 134; and a fastening system comprising an array of prongs 22 manufactured according to the method of the present invention and generally multiply designated as 136. The diaper 120 is shown in FIG. 5 to have an outer surface 152, an inner surface 154 opposed to the outer surface 152, a first waist region 156, a second waist region 158 opposed to the first waist region 156, a crotch region 159 positioned between the first waist region 156 and the second waist region 158, and a periphery 160 which is defined by the outer edges of the diaper 120 in which the longitudinal edges are designated 162 and the end edges are designated 164. The inner surface 154 of the diaper 120 comprises that portion of the diaper 120 which is positioned adjacent to the wearer's body during use (i.e., the inner surface 154 generally is formed by at least a portion of the topsheet 124 and other components joined to the topsheet 124). The outer surface 152 comprises that portion of the diaper 120 which is positioned away from the wearer's body (i.e., the outer surface 152 generally is formed by at least a portion of the backsheet 126 and other components joined to the backsheet 126).

FIG. 5 shows a preferred embodiment of the diaper 120 in which the topsheet 124 and the backsheet 126 have length and width dimensions generally larger than those of the absorbent core 128. The topsheet 124 and the backsheet 126 extend beyond the edges of the absorbent core 128 to thereby form the periphery 160 of the diaper 120. While the topsheet 124, the backsheet 126, and the absorbent core 128 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; and U.S. patent application Ser. No. 07/715,152, allowed, "Absorbent Article With Dynamic Elastic Waist Feature Having A Predisposed Resilient Flexural Hinge", Kenneth B. Buell et al. filed Jun. 13, 1991; each of which is incorporated herein by reference.

The absorbent core 128 may be any absorbent means which is generally compressible, conformable, non-irritating to the wearer's skin, and capable of absorbing and retaining liquids such as urine and other certain body exudates. As shown in FIG. 5, the absorbent core 128 has a garment surface, a body surface, side edges, and waist edges. The absorbent core 128 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 128 should, however, be compatible with the design loading and the intended use of the diaper 120. Further, the size and absorbent capacity of the absorbent core 128 may be varied to accommodate wearers ranging from infants through adults. Exemplary absorbent structures for use as the absorbent core 128 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. Each of these patents are incorporated herein by reference. A preferred embodiment of the diaper 120 has an asymmetric, modified T-shaped, absorbent core 128 having ears 102 in the first waist region 156 but a generally rectangular shape in the second waist region 158. This configuration allows wider elasticized side panels 130 in the second waist region 158.

The backsheet 126 is positioned adjacent the garment surface of the absorbent core 128 and is preferably joined thereto by attachment means (not shown) such as those well known in the art. For example, the backsheet 126 may be secured to the absorbent core 128 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 126 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 126 prevents the exudates absorbed and contained in the absorbent core 128 from wetting articles which contact the diaper 120 such as bedsheets and undergarments. The backsheet 126 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 millimeter (0.5 mil) to about 0.051 millimeter (2.0 mils). Particularly preferred materials for the backsheet include polyethylene films. The backsheet 126 is preferably embossed and/or matte finished to provide a more cloth-like appearance. Further, the backsheet 126 may permit vapors to escape from the absorbent core 128 (i.e., breathable) while still preventing exudates from passing through the backsheet 126.

The topsheet 124 is positioned adjacent the body surface of the absorbent core 128 and is preferably joined thereto and to the backsheet 126 by attachment means (not shown) such as those well known in the art. Suitable attachment means are described with respect to joining the backsheet 126 to the absorbent core 128. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 124 and the backsheet 126 are joined directly to each other in the diaper periphery 160 and are indirectly joined together by directly joining them to the absorbent core 128 by the attachment means (not shown).

The topsheet 124 is compliant, soft feeling, and non-irritating to the wearer's skin. Further, the topsheet 124 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 124 is made of a hydrophobic material to isolate the wearer's skin from liquids contained in the absorbent core 128. There are a number of manufacturing techniques which may be used to manufacture the topsheet 124. For example, the topsheet 124 may be a nonwoven web of fibers spunbonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company, of Walpole, Mass. under the designation P-8.

The diaper 120 preferably further comprises elasticized leg cuffs 132 for providing improved containment of liquids and other body exudates. Each elasticized leg cuff 132 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. While each elasticized leg cuff 132 may be configured so as to be similar to any of the leg bands, side flaps, barrier cuffs, or elastic cuffs described above, it is preferred that each elasticized leg cuff 132 comprise at least an inner barrier cuff 184 comprising a barrier flap 185 and a spacing elastic member 186 such as described in the above-referenced U.S. Pat. No. 4,909,803. In a preferred embodiment as shown in FIG. 5, the elasticized leg cuff 132 additionally comprises an elastic gasketing cuff 104 with one or more elastic strands 105, positioned outboard of the barrier cuff 184 such as described in the above-referenced U.S. Pat. No. 4,695,278.

The diaper 120 preferably further comprises an elastic waist feature 134 that provides improved fit and containment. The elastic waist feature 134 is that portion or zone of the diaper 120 which is intended to elastically expand and contract to dynamically fit the wearer's waist. The elastic waist feature 134 at least extends longitudinally outwardly from at least one of the waist edges of the absorbent core 128 and generally forms at least a portion of the end edge 164 of the diaper 120. Disposable diapers are generally constructed so as to have two elastic waist features, one positioned in the first waist region and one positioned in the second waist region, although diapers can be constructed with a single elastic waist feature. Further, while the elastic waist feature or any of its constituent elements can comprise a separate element affixed to the diaper 120, the elastic waist feature 134 is preferably constructed as an extension of other elements of the diaper such as the backsheet 126 or the topsheet 124, preferably both the backsheet 126 and the topsheet 124. The elasticized waistband 134 may be constructed in a number of different configurations including those described in U.S. Pat. No. 4,515,595 issued to Kievit et al. on May 7, 1985 and the above referenced U.S. patent application Ser. No 07/715,152; each of these references being incorporated herein by reference.

In a preferred embodiment, the diaper also comprises elasticized side panels 130 disposed in the second waist region 158. (As used herein, the term "disposed" is used to mean that an element(s) of the diaper is formed (joined and positioned) in a particular place or position as a unitary structure with other elements of the diaper or as a separate element joined to another element of the diaper.) The elasticized side panels 130 provide an elastically extensible feature that provides a more comfortable and contouring fit by initially conformably fitting the diaper to the wearer and sustaining this fit throughout the time of wear well past when the diaper has been loaded with exudates since the elasticized side panels allow the sides of the diaper to expand and contract. The elasticized side panels 130 further provide more effective application of the diaper 120 since even if the diaperer pulls one elasticized side panel 130 farther than the other during application (asymmetrically), the diaper 120 will "self-adjust" during wear. While the diaper 120 of the present invention preferably has the elasticized side panels 130 disposed in the second waist region 158; alternatively, the diaper 120 may be provided with elasticized side panels 130 disposed in the first waist region 156 or in both the first waist region 156 and the second waist region 158. While the elasticized side panels 130 may be constructed in a number of configurations, examples of diapers with elasticized side panels positioned in the ears (ear flaps) of the diaper are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and the hereinbefore referenced U.S. patent application Ser. No. 07/715,152; each of which are incorporated herein by reference. The preferred elasticized side panels comprise the zero strain stretch laminate described in the hereinbefore referenced U.S. patent application Ser. No. 07/715,152.

The diaper 120 is further provided with a fastening system 136 for forming a waist closure. The fastening system 136 maintains the first waist region 156 and the second waist region 158 in an overlapping configuration to maintain the diaper on the wearer. The fastening system 136 comprises at least an array of prongs 22 manufactured according to the method of the present invention, which is engageable with a complementary receiving surface such as a loop fastening material or a nonwoven material such as the material which forms the topsheet 124. While the fastening system 136 may be constructed in a number of configurations, examples of diapers with mechanical fastening systems are disclosed in U.S. Pat. No. 4,869,724 entitled "Mechanical Fastening Systems With Adhesive Tape Disposal Means For Disposable Absorbent Articles" issued to Scripps on Sep. 26, 1989; U.S. Pat. No. 4,846,815 entitled "Disposable Diaper Having An Improved Fastening Device" issued to Scripps on Jul. 11, 1989; and U.S. Pat. No. 4,894,060 entitled "Disposable Diaper With Improved Hook Fastener Portion" issued to Nestegard on Jan. 16, 1990. A fastening system having combination adhesive/mechanical closure elements is described in U.S. Pat. No. 4,946,527 entitled "Pressure-Sensitive Adhesive Fastener And Method of Making Same" issued to Battrell on Aug. 7, 1990. Each of these patents are incorporated herein by reference. A preferred fastening system configuration is a two point fastening system described in U.S. patent application Ser. No. 07/714,476, entitled "Absorbent Article with Fastening System Providing Dynamic Elasticized Waistband Fit", filed Jun. 13, 1991 in the name of Weil et al., which patent application is incorporated herein by reference.

The preferred two point fastening system, or dual tension fastening system 136, shown in FIG. 5 and 6, comprises a primary fastening system 138 for providing the side closure and a waist closure system 140 for providing the waist closure. The primary fastening system 138 maintains the first waist region 156 and the second waist region 158 in an overlapping configuration such that lateral tensions are maintained around the circumference of the diaper to maintain the diaper on the wearer. The waist closure system 140 forms a waist closure that dynamically maintains/creates lateral tensions through the elasticized waistband 134 so as to improve the fit and containment characteristics of the diaper 120 by reducing gapping, sagging, and rollover of the elasticized waistband 134.

As shown in FIG. 5, the primary fastening system 138 comprises a securement member 142 disposed adjacent each longitudinal edge 162 in the second waist region 158, and at least one landing member 144 disposed in the first waist region 156 so as to form a portion of the outer surface 152. Each securement member 142 preferably comprises a tape tab 192 and a first fastening component 112. The landing member 144 preferably comprises a complementary second fastening component 114 engageable with the first fastening component 112 of the securement member 142. An exemplary primary fastening system wherein the first and second fastening components each comprise mechanical closure elements comprising hook and loop fastening materials is disclosed in U.S. Pat. No. 4,869,724 entitled "Mechanical Fastening Systems With Adhesive Tape Disposal Means For Disposable Absorbent Articles" issued to Scripps on Sep. 26, 1989. Primary fastening systems utilizing mechanical closure elements are also disclosed in U.S. Pat. No. 4,846,815 entitled "Disposable Diaper Having An Improved Fastening Device" issued to Scripps on Jul. 11, 1989; and U.S. Pat. No. 4,894,060 entitled "Disposable Diaper With Improved Hook Fastener Portion" issued to Nestegard on Jan. 16, 1990. A primary fastening system having combination adhesive/mechanical closure elements is described in U.S. Pat. No. 4,946,527 entitled "Pressure-Sensitive Adhesive Fastener And Method of Making Same" issued to Battrell on Aug. 7, 1990. Each of these patents are incorporated herein by reference. In a preferred embodiment of the present invention as is shown in FIG. 5, the primary fastening system 138 comprises an adhesive tape tab fastening system comprising a tape tab 192 having an adhesive attachment layer 196 and a landing member 144 comprising a reinforcing strip 116 joined to the backsheet 126. Examples of such adhesive tape tab fastening systems are disclosed in U.S. Pat. No. 3,848,594 entitled "Tape Fastening System for Disposable Diaper" issued to Buell on Nov. 19, 1974; and the adhesive tape tabs, reinforcing strip, and indicia means disclosed in U.S. Pat. No. B1 4,662,875 entitled "Absorbent Article" issued to Hirotsu and Robertson on May 5, 1987. Each of these patents are incorporated herein by reference.

When the first fastening component 112 of the securement member 142 comprises an adhesive attachment layer 196, the second fastening component 114 of the landing member 144 preferably comprises a reinforcing strip 116 and/or the backsheet 126. When the first fastening component 112 of the securement member 142 comprises a mechanical closure element, the second fastening component 114 also comprises a mechanical closure element. Thus, when the first fastening component 112 comprises a hook fastening material, such as the fastening material of the present invention, the second fastening component 114 preferably comprises a loop fastening material.

In a preferred embodiment of the present invention as shown in FIG. 5, the landing member 144 preferably comprises a reinforcing strip 116 releasably engageable with the adhesive attachment layer 196 of the tape tabs 192. The reinforcing strip 116 may comprise any of a number of configurations and materials secured to the backsheet 126 of the diaper 120. The reinforcing strip 116 is preferably a separate member secured to the backsheet 126 to form a portion of the outer surface 152 of the diaper 120. A preferred reinforcing strip 116 comprises a sheet of biaxially oriented polypropylene film.

The dual tension fastening system 136 additionally comprises a waist closure system 140 for providing a waist closure adjacent the end edge 164 of the diaper 120. The waist closure anchors a portion of the span of the end edge 164. Further, when the diaper 120 comprises an elasticized waistband 134, the waist closure dynamically creates/maintains lateral tensions through the elasticized waistband 134.

The waist closure anchors a portion of the span of the end edge 164 of the diaper 120, preferably a portion of the extensible span of the elasticized waistband 134. (i.e., The first and second attachment components of the waist closure system 140 act to anchor the positional relationship of the elasticized waistband 134 with the elasticized side panels 130.) The term "anchor" is used herein to mean that the attachment components provide an adjustable positioning fastener that achieves a closure with sufficient shear resistance so that there is little or no shear slippage or movement between the attachment components once the closure is achieved. The positional relationship of the elasticized waistband 134 with the elasticized side panels 130 (i.e., the geometric relationship between the anchor zones of the first attachment components 146) establishes a defined waist circumferential dimension adjacent the end edge 164 of the diaper 120 which is distinct (longitudinally spaced) from the circumferential dimension established by the side closure formed by the primary fastening system 138.

The waist closure also creates/maintains lateral tension(s) through the elasticized waistband 134. The waist closure contributes some portion of an initial pretension (lateral tension) within the elasticized waistband 134 that allows the elasticized waistband 134 to snugly fit against the wearer's waist when initially fitted. The elasticized waistband 134 maintains, during use, some portion of the pretension created within it by the waist closure. Since the elasticized waistband maintains some portion of the pretension created within it, the elasticized waistband can repeatedly elastically expand or contract with the motions of the wearer so as to snugly sustain the fit of the diaper against the wearer's waist throughout use.

As shown in FIG. 5, the waist closure system 140 comprises at least one, preferably a pair of, first attachment component(s) 146 and at least one second attachment component 148. As shown in FIG. 5, the first attachment component(s) 146 are longitudinally aligned with the elasticized waistband 134 so that the lateral tensions dynamically created/maintained by the waist closure system 140 extends in and through the elasticized waistband 134 during use. Further, the attachment components of the waist closure system 140 are longitudinally spaced from the securement members 142 and the landing member 144 of the primary fastening system 138 to provide a distinct, defined waist circumferential dimension for the diaper and two distinct zones of lateral tension(s). The zone of tension created by the primary fastening system 38 secures the garment on the wearer while the zone of tension dynamically created/maintained by the waist closure system 140 dynamically maintains the upper waist closure during wear.

The attachment components of the waist closure system 140, preferably comprise an array of prongs 22 of the present invention. In a preferred embodiment shown in FIGS. 5 & 6, the first attachment component 146 will comprise an array of prongs 22 and the second attachment component 148 will comprise a loop fastening material having fibrous elements. The array of prongs 22 is intended to mechanically engage the fibrous elements of the loop fastening material so as to provide a secure closure. The loop fastening material provides a plurality of fibrous elements that engage the engaging elements of the prongs 22. The loop fastening material may be manufactured from a wide range of materials to provide fibrous elements, preferably loops. Such suitable materials include nylon, polyester, polypropylene, any combination of these materials, or other materials as are known in the art. A suitable loop fastening material comprises a number of fiber loops projecting from a backing such as the commercially available material designated "Scotchmate" brand nylon woven loop No. SJ3401 available from Minnesota Mining and Manufacturing Company, St. Paul, Minn. Another commercially available loop fastening material comprises a tricot knit fabric having a plurality of nylon filament loops projecting from a backing of nylon such as the commercially available material designated "Guilford No. 16110" available from Guilford Mills of Greensboro, N.C. An exemplary inexpensive loop fastening material and a method of making such a loop fastening material are described in European Patent Application 0 289 198; The Procter & Gamble Company, published Nov. 2, 1988, which application is incorporated herein by reference. A suitable loop fastening material may also be a woven or nonwoven fabric or any other type of fibrous material or loop material which are well known in the art. Examples of nonwoven materials suitable for use as a loop fastening material are discussed herein with respect to the materials useful as the topsheet 124 of the diaper 120. In a preferred embodiment, the loop fastening material is formed by the nonwoven material of the topsheet 124.

The diaper 120 additionally comprises a positioning patch 150 located subjacent the first attachment component 146. The positioning patch 150 raises the first attachment component 146 in the Z direction (thickness) to allow the first attachment component 146 to come in better contact with the second attachment component 148 and allow the waist closure system to more easily be closed (with less effort). The positioning patch 150 also provides a zone of increased flexural stiffness that reduces the tendency of the flexible ear flaps 188 to fold over onto the first attachment component(s) 146 thereby occluding the prongs 22 from being secured during diaper application. Thus, the positioning patch 150 can comprise any element that provides a Z direction build up to the first attachment components 146. As shown in FIG. 5, the positioning patches 150 each comprise a rectangular-shaped piece of material positioned subjacent the first attachment component 146. While the positioning patches 150 may be positioned directly subjacent the first attachment components 146, the positioning patches 150 are preferably positioned between the topsheet 124 and the backsheet 126 as shown in FIG. 6. In order to provide a flexurally stiff circumference about the waist of the wearer, the lateral edges of the positioning patches can be abutted to or slightly overlapped with the side edges 175 of the elastic waistband member 176. The positioning patches 150 preferably comprise a 38 millimeter wide by 32 millimeter long patch of elastomeric foam. More preferably, during manufacture of the diaper, the positioning patches 150 are formed of the same material as the elastic side panel member 190 with the elastic side panel member 190 of one diaper and the positioning patch 150 of the adjacent diaper being formed from the same segment of material that is then cut after the diaper is completed. Thus, the positioning patch 150 extends from the end edge 164 of the diaper 120 inward toward the center of the diaper 120.

The diaper 120 is preferably applied to a wearer by positioning one of the waist regions, preferably the second waist region 158, under the wearer's back and drawing the remainder of the diaper between the wearer's legs so that the other waist region, preferably the first waist region 156, is positioned across the front of the wearer. The tape tabs of the fastening system are then released from the release portion. The diaperer then wraps the elasticized side panel around the wearer, while still grasping the tab portion. The elasticized side panels will typically be extended and tensioned during this operation so as to conform to the size and shape of the wearer. The fastening system is secured to the outer surface of the diaper to effect a side closure.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin friendly hook fastening material for use as a component of a mechanical fastening system, said hook fastening material comprising:
   a substrate comprising a compressible material, wherein said substrate is comprised of fluid impervious top layer, a fluid impervious bottom layer joined to said top layer to form at least one pocket, and a compressible fluid positioned within said pocket; and an array of prongs, said array comprising from 1600 to 2500 prongs per square inch, each of said prongs comprising a base joined to said substrate, an engaging means, and a shank comprising a proximal end joined to said base and a distal end joined to said engaging means.

2. The hook fastening material of claim 1 wherein at least one of said prongs has an included angle $\theta$ of between 90° to 160°.

3. The hook fastening material of claim 1 wherein at least one of said prongs has an included angle $\theta$ of between 100° to 150°.

4. The hook fastening material of claim 1 wherein at least one of said prongs has an included angle $\theta$ of between 100° to 140°.

5. The hook fastening material of claim 1 wherein each of said prongs is comprised of an ethylene vinyl acetate based polymer.

6. The hook fastening material of claim 1 wherein each of said prongs is comprised of a polyethylene based polymer.

7. The hook fastening material of claim 1 wherein each of said prongs is comprised of an ethylene vinyl acetate based polymer.

8. The hook fastening material of claim 1 wherein each of said prongs is comprised of a polyethylene based polymer.

9. The hook fastening of claim 1 wherein at least one of said prongs has an included angle $\theta$ of between 90° to 160°.

10. The hook fastening material of claim 7 wherein at least one of said prongs has an included angle $\theta$ of between 90° to 160°.

* * * * *